US012761554B2

(12) United States Patent
Aqad et al.

(10) Patent No.: US 12,761,554 B2
(45) Date of Patent: Oct. 13, 2026

(54) PHOTOACTIVE COMPOUNDS, PHOTORESIST COMPOSITIONS INCLUDING THE SAME, AND PATTERN FORMATION METHODS

(71) Applicant: ROHM AND HAAS ELECTRONIC MATERIALS LLC, Marlborough, MA (US)

(72) Inventors: Emad Aqad, Northborough, MA (US); Tomas Marangoni, Marlborough, MA (US); Yinjie Cen, Shrewsbury, MA (US); Paul J. LaBeaume, Auburn, MA (US); Mingqi Li, Shrewsbury, MA (US); James F. Cameron, Brookline, MA (US)

(73) Assignee: ROHM AND HAAS ELECTRONIC MATERIALS LLC, Marlborough, MA (US)

( * ) Notice: Subject to any disclaimer, the term of this patent is extended or adjusted under 35 U.S.C. 154(b) by 601 days.

(21) Appl. No.: 18/352,646

(22) Filed: Jul. 14, 2023

(65) Prior Publication Data

US 2024/0027904 A1 Jan. 25, 2024

Related U.S. Application Data

(60) Provisional application No. 63/389,212, filed on Jul. 14, 2022.

(51) Int. Cl.

*G03F 7/004* (2006.01)
*C07D 275/06* (2006.01)
*C07D 417/06* (2006.01)

(52) U.S. Cl.

CPC ......... *G03F 7/0045* (2013.01); *C07D 275/06* (2013.01); *C07D 417/06* (2013.01)

(58) Field of Classification Search

None

See application file for complete search history.

(56) References Cited

U.S. PATENT DOCUMENTS

| | | | | |
|---|---|---|---|---|
| 4,189,323 | A | 2/1980 | Buhr | |
| 5,874,616 | A | 2/1999 | Howells et al. | |
| 6,136,500 | A | 10/2000 | Kobayashi et al. | |
| 6,485,883 | B2 | 11/2002 | Kodama et al. | |
| 6,605,409 | B2 | 8/2003 | Kodama et al. | |
| 8,431,325 | B2 | 4/2013 | Hashimoto et al. | |
| 9,488,910 | B2 | 11/2016 | Liu et al. | |
| 2002/0004570 | A1* | 1/2002 | Zampini | C08F 32/08 526/260 |
| 2002/0006578 | A1 | 1/2002 | Kodama et al. | |
| 2003/0008241 | A1 | 1/2003 | Sato et al. | |
| 2011/0092384 | A1* | 4/2011 | Kwon | C07K 7/64 530/323 |

FOREIGN PATENT DOCUMENTS

| | | | | |
|---|---|---|---|---|
| EP | 1635218 A2 | | 3/2006 | |
| JP | 2001330947 A | * | 11/2001 | G03F 7/0045 |

(Continued)

OTHER PUBLICATIONS

S. P. Conway et al., S. P. Conway et al. "Benzylammonium 2,4-bis(dicyanomethylene)-2,3-dihydroisoindolide".Acta Cryst., 2005, vol. E61, pp. 2258-o2260.

F. Closs et al., F. Closs et al. "2,6-Diaza-s-indacenes". Angew Chem. Inr. Ed. Engl., 1987, vol. 26, No. 10, pp. 1037-1039.

Lee, D., et al. "Perflourosulfonyl imides andmethides: investigating the lithographic potential of novel superacid PAGs", Proceedings of SPIE, vol. 4690, Jul. 24, 2002, 10 pages.

Wellman, D., et al. "An Anthrylidenequinodiquinocyclopropane and Related Compounds. Their Structure and Phsyical Properties" J. Org. Chem, 1984, 49, 965-971.

Wilson, S. et al. A New Reaction in Organosilicon Chemistry: The Oxidative Fragmentation of Y-Hydroxy Silanes, Tetrahedron Letters, vol. 26, No. 16, pp. 1969-1972, 1985.

(Continued)

*Primary Examiner* — Anca Eoff

(74) *Attorney, Agent, or Firm* — CANTOR COLBURN LLP

(57) ABSTRACT

A photoactive compound including an organic cation; and an anion represented by Formula (1):

(1)

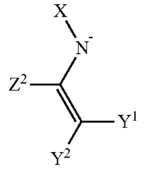

wherein X is an organic group; $Y^1$ and $Y^2$ are each independently a non-hydrogen substituent; $Y^1$ and $Y^2$ together optionally form a ring; $Z^2$ is hydrogen, halogen, substituted or unsubstituted $C_{1-30}$ alkyl, substituted or unsubstituted $C_{3-30}$ cycloalkyl, substituted or unsubstituted $C_{3-30}$ heterocycloalkyl, substituted or unsubstituted $C_{6-50}$ aryl, substituted or unsubstituted $C_{7-50}$ arylalkyl, substituted or unsubstituted $C_{7-50}$ alkylaryl, substituted or unsubstituted $C_{6-50}$ aryloxy, substituted or unsubstituted $C_{3-30}$ heteroaryl, substituted or unsubstituted $C_{4-30}$ alkylheteroaryl, substituted or unsubstituted $C_{4-30}$ heteroarylalkyl, or substituted or unsubstituted $C_{3-30}$ heteroaryloxy; $Z^2$ optionally further comprises one or more divalent linking groups as part of its structure; $Z^2$ and one of $Y^1$ or $Y^2$ together optionally form a ring; X and $Z^2$ together optionally form a ring; and X and one of $Y^1$ or $Y^2$ together optionally form a ring.

12 Claims, No Drawings

(56) References Cited

FOREIGN PATENT DOCUMENTS

| | | | |
|---|---|---|---|
| JP | 2005208134 | A | 8/2005 |
| JP | 2013250431 | A | 12/2013 |
| WO | 2021200178 | A1 | 10/2021 |
| WO | 2021235283 | A1 | 11/2021 |

OTHER PUBLICATIONS

Closs et al., "2,6-Diaza-s-indacenes," Angew. Chem. Int. Ed. Engl., 1987, pp. 1037-1039, vol. 26, No. 10.
Conway et al., "Benzyl•ammonium 2,4-bi•••(di•cyan••methy••ene)-2,3-di•hydro•isoindolide," Acta Cryst., 2005, pp. o2258-o2260, E61.

* cited by examiner

PHOTOACTIVE COMPOUNDS, PHOTORESIST COMPOSITIONS INCLUDING THE SAME, AND PATTERN FORMATION METHODS

CROSS REFERENCE TO RELATED APPLICATIONS

This application claims the benefit of and priority to U.S. Provisional Application Ser. No. 63/389,212 filed Jul. 14, 2022, the entire content of which is incorporated herein by reference.

FIELD

The present invention relates to photoactive compounds for photoresist compositions and to pattern formation methods using such photoresist compositions. The invention finds applicability in lithographic applications in the semiconductor manufacturing industry.

BACKGROUND

Photoresist materials are photosensitive compositions typically used for transferring an image to one or more underlying layers such as a metal, semiconductor or dielectric layer disposed on a semiconductor substrate. To increase the integration density of semiconductor devices and allow for the formation of structures having dimensions in the nanometer range, photoresists and photolithography processing tools having high-resolution capabilities have been and continue to be developed.

Chemically amplified photoresists are conventionally used for high-resolution processing. Such resists typically employ a polymer having acid-labile groups, a photoacid generator and an acid quenching material. Pattern-wise exposure to activating radiation through a photomask causes the acid generator to form an acid which, during post-exposure baking, causes cleavage of the acid-labile groups in exposed regions of the polymer. Acid quenching materials are often added to the photoresist composition for controlling the diffusion of the acid to unexposed region to improve the contrast. The result of the lithographic process is the creation of difference in solubility characteristics between exposed and unexposed regions of the resist in a developer solution. In a positive tone development (PTD) process, exposed regions of the photoresist layer become soluble in the developer and are removed from the substrate surface, whereas unexposed regions, which are insoluble in the developer, remain after development to form a positive image. The resulting relief image permits selective processing of the substrate.

Non-photoactive acid quenching materials that are commonly used in chemically amplified resist include linear aliphatic amines, cyclic aliphatic amines, aromatic amines, linear and cyclic amides, and derivatives thereof. Another type of commonly used acid quenching material class is photoactive quenchers, known as photodecomposable quencher or photodegradable quencher. Photoactive quenchers have also been used in chemically amplified resist compositions. A photodecomposable quencher is typically a salt comprising a photoactive onium cation and an anion, wherein the anion is the conjugated base of weak acid. The salt functions as a base or acid quencher before exposure. Upon exposure, the anion part of the photodegradable quencher becomes protonated and therefore becomes more acidic. Therefore, upon irradiation of chemically amplified resist that comprises photodecomposable quencher, the concentration of the acid quencher in the exposed area decreased dramatically. On the other hand, the intact photodecomposable quencher in the unexposed area may trap acid molecules that diffuse from the exposed area during lithographic processing, thereby improving lithographic performance.

Photoresist compositions including photodecomposable quenchers and their use have been described in the art. The need exists for new photoresists that can provide highly resolved line-space features with superior contrast and/or contact-holes (CH) with improved critical dimension uniformity (CDU).

SUMMARY

Provided is a photoactive compound including an organic cation; and an anion represented by Formula (1):

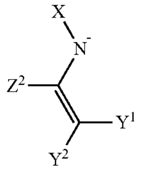

(1)

wherein X is an organic group; $Y^1$ and $Y^2$ are each independently a non-hydrogen substituent; $Y^1$ and $Y^2$ together optionally form a ring; $Z^2$ is hydrogen, halogen, substituted or unsubstituted $C_{1-30}$ alkyl, substituted or unsubstituted $C_{3-30}$ cycloalkyl, substituted or unsubstituted $C_{3-30}$ heterocycloalkyl, substituted or unsubstituted $C_{6-50}$ aryl, substituted or unsubstituted $C_{7-50}$ arylalkyl, substituted or unsubstituted $C_{7-50}$ alkylaryl, substituted or unsubstituted $C_{6-50}$ aryloxy, substituted or unsubstituted $C_{3-30}$ heteroaryl, substituted or unsubstituted $C_{4-30}$ alkylheteroaryl, substituted or unsubstituted $C_{4-30}$ heteroarylalkyl, or substituted or unsubstituted $C_{3-30}$ heteroaryloxy; $Z^2$ optionally further comprises one or more divalent linking groups as part of its structure; $Z^2$ and one of $Y^1$ or $Y^2$ together optionally form a ring; X and $Z^2$ together optionally form a ring; and X and one of $Y^1$ or $Y^2$ together optionally form a ring.

Also provided is a photoresist composition including the photoactive compound and a polymer.

Also provided is a patterning method including applying a layer of the photoresist composition of claim 9 or 10 on a substrate to provide a photoresist composition layer; pattern-wise exposing the photoresist composition layer to activating radiation to provide an exposed photoresist composition layer; and developing the exposed photoresist composition layer.

DETAILED DESCRIPTION

Reference will now be made in detail to exemplary embodiments, examples of which are illustrated in the present description. In this regard, the present exemplary embodiments may have different forms and should not be construed as being limited to the descriptions set forth herein. Accordingly, the exemplary embodiments are merely described below, by referring to the figures, to explain aspects of the present description. As used herein, the term "and/or" includes any and all combinations of one or more of the associated listed items. Expressions such as "at least one of," when preceding a list of elements, modify the entire list of elements and do not modify the individual elements of the list.

As used herein, the terms "a," "an," and "the" do not denote a limitation of quantity and are to be construed to cover both the singular and the plural, unless otherwise indicated herein or clearly contradicted by context. "Or" means "and/or" unless clearly indicated otherwise. The modifier "about" used in connection with a quantity is inclusive of the stated value and has the meaning dictated by the context (e.g., includes the degree of error associated with measurement of the particular quantity). All ranges disclosed herein are inclusive of the endpoints, and the endpoints are independently combinable with each other. The suffix "(s)" is intended to include both the singular and the plural of the term that it modifies, thereby including at least one of that term. "Optional" or "optionally" means that the subsequently described event or circumstance can or cannot occur, and that the description includes instances where the event occurs and instances where it does not. The terms "first," "second," and the like, herein do not denote an order, quantity, or importance, but rather are used to distinguish one element from another. When an element is referred to as being "on" another element, it may be directly in contact with the other element or intervening elements may be present therebetween. In contrast, when an element is referred to as being "directly on" another element, there are no intervening elements present. It is to be understood that the described components, elements, limitations, and/or features of aspects may be combined in any suitable manner in the various aspects.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

As used herein, "actinic rays" or "radiation" means, for example, a bright line spectrum of a mercury lamp, far ultraviolet rays represented by an excimer laser, extreme ultraviolet rays (EUV light), X-rays, particle rays such as electron beams and ion beams, or the like. In addition, in the present invention, "light" means actinic rays or radiation. The krypton fluoride laser (KrF laser) is a particular type of excimer laser, which is sometimes referred to as an exciplex laser. "Excimer" is short for "excited dimer," while "exciplex" is short for "excited complex." An excimer laser uses a mixture of a noble gas (argon, krypton, or xenon) and a halogen gas (fluorine or chlorine), which under suitable conditions of electrical stimulation and high pressure, emits coherent stimulated radiation (laser light) in the ultraviolet range. Furthermore, "exposure" in the present specification includes, unless otherwise specified, not only exposure by a mercury lamp, far ultraviolet rays represented by an excimer laser, X-rays, extreme ultraviolet rays (EUV light), or the like, but also writing by particle rays such as electron beams and ion beams.

A used herein, an "organic group" includes one or more carbon atoms, for example 1 to 60 carbon atoms. The term "hydrocarbon" refers to an organic compound or to an organic group having at least one carbon atom and at least one hydrogen atom. The term "alkyl" refers to a straight or branched chain saturated hydrocarbon group having the specified number of carbon atoms and having a valence of one; "alkylene" refers to an alkyl group having a valence of two; "hydroxyalkyl" refers to an alkyl group substituted with at least one hydroxyl group (—OH); "alkoxy" refers to "alkyl-O—"; "carboxyl" and "carboxylic acid group" refer to a group having the formula "—C(═O)—OH"; "cycloalkyl" refers to a monovalent group having one or more saturated rings in which all ring members are carbon; "cycloalkylene" refers to a cycloalkyl group having a valence of two; "alkenyl" refers to a straight or branched chain, monovalent hydrocarbon group having at least one carbon-carbon double bond; "alkenoxy" refers to "alkenyl-O—"; "alkenylene" refers to an alkenyl group having a valence of two; "cycloalkenyl" refers to a non-aromatic cyclic divalent hydrocarbon group having at least three carbon atoms, with at least one carbon-carbon double bond; "alkynyl" refers to a monovalent hydrocarbon group having at least one carbon-carbon triple bond; the term "aromatic group" refers to a monocyclic or polycyclic ring system that satisfies the Huckel Rule and includes carbon atoms in the ring, and optionally may include one or more heteroatoms selected from N, O, and S instead of a carbon atom in the ring; "aryl" refers to a monovalent aromatic monocyclic or polycyclic ring system where every ring member is carbon, and may include a group with an aromatic ring fused to at least one cycloalkyl or heterocycloalkyl ring; "arylene" refers to an aryl group having a valence of two; "alkylaryl" refers to an aryl group that has been substituted with an alkyl group; "arylalkyl" refers to an alkyl group that has been substituted with an aryl group; "aryloxy" refers to "aryl-O—"; and "arylthio" refers to "aryl-S—".

The prefix "hetero" means that the compound or group includes at least one member that is a heteroatom (e.g., 1, 2, 3, or 4 or more heteroatom(s)) instead of a carbon atom, wherein the heteroatom(s) is each independently N, O, S, Si, or P; "heteroatom-containing group" refers to a substituent group that includes at least one heteroatom; "heteroalkyl group" refers to an alkyl group having 1-4 or more heteroatoms instead of carbon; "heterocycloalkyl group" refers to a cycloalkyl group having 1-4 or more heteroatoms as ring members instead of carbon; "heterocycloalkylene group" refers to a heterocycloalkyl group having a valence of two; "heteroaryl group" refers to an aryl group having 1-4 or more heteroatoms as ring members instead of carbon; and "heteroarylene group" refers to an heteroaryl group having a valence of two.

Each of the foregoing substituent groups optionally may be substituted unless expressly provided otherwise. For example, where the group is cited without specifying that it is substituted or unsubstituted, the group includes both a group having no substituent and a group having a substituent. The term "optionally substituted" refers to being substituted or unsubstituted.

"Substituted" means that at least one hydrogen atom of the chemical structure is replaced with another terminal substituent group that is typically monovalent, provided that the designated atom's normal valence is not exceeded. When the substituent is oxo (i.e., ═O), then two geminal hydrogen atoms on the carbon atom are replaced with the terminal oxo group. Combinations of substituents or variables are permissible. Exemplary substituent groups that may be present on a "substituted" position include, but are not limited to, nitro (—$NO_2$), cyano (—CN), hydroxyl (—OH), oxo (═O), amino (—$NH_2$), mono- or di-($C_{1-6}$)alkylamino, alkanoyl (such as a $C_{2-6}$ alkanoyl group such as acyl), formyl (—C(═O)H), carboxylic acid or an alkali metal or ammonium salt thereof; esters (including acrylates, methacrylates, and lactones) such as $C_{2-6}$ alkyl esters (—C(═O)O-alkyl or —OC(═O)-alkyl) and $C_{7-13}$ aryl esters (—C(═O)O-aryl or —OC(═O)-aryl), amido (—C(═O)$NR_2$ wherein R is hydrogen or $C_{1-6}$ alkyl), carboxamido (—$CH_2C$(═O)$NR_2$ wherein R is hydrogen or $C_{1-6}$ alkyl), halogen, thiol (—SH), $C_{1-6}$ alkylthio (—S-alkyl), thiocyano (—SCN), $C_{1-6}$ alkyl, $C_{2-6}$ alkenyl, $C_{2-6}$ alkynyl, $C_{1-6}$ haloalkyl, $C_{1-9}$ alkoxy, $C_{1-6}$ haloalkoxy, $C_{3-12}$ cycloalkyl, $C_{5-18}$ cycloalkenyl, $C_{2-18}$ heterocycloalkenyl, $C_{6-12}$ aryl having at least one aromatic ring (e.g., phenyl, biphenyl, naphthyl, or the like, each ring either substituted or unsubstituted aromatic), $C_{7-19}$ arylalkyl having 1 to 3 separate or fused rings and from 6 to 18 ring carbon atoms, arylalkoxy having 1 to 3 separate or fused rings and from 6 to 18 ring carbon atoms, $C_{7-12}$ alkylaryl, $C_{3-12}$ heterocycloalkyl, $C_{3-12}$ heteroaryl, $C_{1-6}$ alkyl sulfonyl (—S(═O)$_2$-alkyl), $C_{6-12}$ arylsulfonyl (—S(═O)$_2$-aryl), or tosyl ($CH_3C_6H_4SO_2$—).

The term "halogen" means a monovalent substituent that is fluorine (fluoro), chlorine (chloro), bromine (bromo), or iodine (iodo). The prefix "halo" means a group including one or more of a fluoro, chloro, bromo, or iodo substituent instead of a hydrogen atom. A combination of halo groups (e.g., bromo and fluoro), or only fluoro groups may be present. For example, the term "haloalkyl" refers to an alkyl group substituted with one or more halogens. As used herein, "substituted $C_{1-8}$ haloalkyl" refers to a $C_{1-8}$ alkyl group substituted with at least one halogen, and is further substituted with one or more other substituent groups that are not halogens.

As used herein, an "acid-labile group" refers to a group in which a bond is cleaved by the action of an acid, optionally and typically with thermal treatment, resulting in formation of a polar group, such as a carboxylic acid or alcohol group, being formed on the polymer, and optionally and typically with a moiety connected to the cleaved bond becoming disconnected from the polymer. In other systems, a non-polymeric compound may include an acid-labile group that may be cleaved by the action of an acid, resulting in formation of a polar group, such as a carboxylic acid or alcohol group on a cleaved portion of the non-polymeric compound. Such acid is typically a photo-generated acid with bond cleavage occurring during post-exposure baking (PEB); however, embodiments are not limited thereto, and, for example, such acid may be thermally generated. Suitable acid-labile groups include, for example: tertiary alkyl ester groups, secondary or tertiary aryl ester groups, secondary or tertiary ester groups having a combination of alkyl and aryl groups, tertiary alkoxy groups, acetal groups, or ketal groups. Acid-labile groups are also commonly referred to in the art as "acid-cleavable groups," "acid-cleavable protecting groups," "acid-labile protecting groups," "acid-leaving groups," "acid-decomposable groups," and "acid-sensitive groups."

As used herein, when a definition is not otherwise provided, a "divalent linking group" refers to a divalent group including one or more of —O—, —S—, —Te—, —Se—, —C(O)—, —N($R^a$)—, —S(O)—, —S(O)$_2$—, —C(S)—, —C(Te)—, —C(Se)—, substituted or unsubstituted $C_{1-30}$ alkylene, substituted or unsubstituted $C_{3-30}$ cycloalkylene, substituted or unsubstituted $C_{3-30}$ heterocycloalkylene, substituted or unsubstituted $C_{6-30}$ arylene, substituted or unsubstituted $C_{3-30}$ heteroarylene, or a combination thereof, wherein $R^a$ is hydrogen, substituted or unsubstituted $C_{1-20}$ alkyl, substituted or unsubstituted $C_{1-20}$ heteroalkyl, substituted or unsubstituted $C_{6-30}$ aryl, or substituted or unsubstituted $C_{3-30}$ heteroaryl. Typically, the divalent linking group includes one or more of —O—, —S—, —C(O)—, —N($R^a$)—, —S(O)—, —S(O)$_2$—, substituted or unsubstituted $C_{1-30}$ alkylene, substituted or unsubstituted $C_{3-30}$ cycloalkylene, substituted or unsubstituted $C_{3-30}$ heterocycloalkylene, substituted or unsubstituted $C_{6-30}$ arylene, substituted or unsubstituted $C_{3-30}$ heteroarylene, or a combination thereof, wherein $R^a$ is hydrogen, substituted or unsubstituted $C_{1-20}$ alkyl, substituted or unsubstituted $C_{1-20}$ heteroalkyl, substituted or unsubstituted $C_{6-30}$ aryl, or substituted or unsubstituted $C_{3-30}$ heteroaryl. More typically, the divalent linking group includes at least one of —O—, —C(O)—, —C(O)O—, —N($R^a$)—, —C(O)N($R^a$)—, substituted or unsubstituted $C_{1-10}$ alkylene, substituted or unsubstituted $C_{3-10}$ cycloalkylene, substituted or unsubstituted $C_{3-10}$ heterocycloalkylene, substituted or unsubstituted $C_{6-10}$ arylene, substituted or unsubstituted $C_{3-10}$ heteroarylene, or a combination thereof, wherein $R^a$ is hydrogen, substituted or unsubstituted $C_{1-10}$ alkyl, substituted or unsubstituted $C_{1-10}$ heteroalkyl, substituted or unsubstituted $C_{6-10}$ aryl, or substituted or unsubstituted $C_{3-10}$ heteroaryl.

The present invention relates to photoactive compounds, for example photodecomposable quencher compounds. In particular, the inventive photoactive compounds are salts including a nitrogen atom anion that is directly bonded to an alkenyl group and optionally directly bonded to a second electron-withdrawing group. The inventive photoactive compounds are particularly useful in photoresist compositions to achieve improved contrast and improved localized critical dimension uniformity (LCDU).

The photoactive compound includes an organic cation and an anion represented by Formula (1):

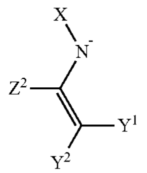

(1)

In Formula (1), X is an organic group. For example, X may include substituted or unsubstituted $C_{1-30}$ alkyl, substituted or unsubstituted $C_{1-30}$ heteroalkyl, substituted or unsubstituted $C_{3-30}$ cycloalkyl, substituted or unsubstituted $C_{3-30}$ heterocycloalkyl, substituted or unsubstituted $C_{2-30}$ alkenyl, substituted or unsubstituted $C_{2-30}$ alkynyl, substituted or unsubstituted $C_1$-$C_{30}$ alkoxy, substituted or unsubstituted $C_1$-$C_{30}$ alkylthio, substituted or unsubstituted $C_3$-$C_{10}$ cycloalkenyl, substituted or unsubstituted $C_3$-$C_{10}$ heterocycloalkenyl, substituted or unsubstituted $C_{6-30}$ aryl, substituted or unsubstituted $C_{7-30}$ arylalkyl, substituted or unsubstituted $C_{7-30}$ alkylaryl, or substituted or unsubstituted $C_6$-$C_{30}$ aryloxy, wherein X may optionally further include one or more divalent linking groups as part of its structure. In some embodiments, X may further include as part of its structure one or more divalent linking groups selected from —O—, —C(O)—, —C(O)O—, —S—, —S(O)$_2$—, —N(R')—, —C(O)N(R')—, substituted or unsubstituted $C_{1-30}$ alkylene, substituted or unsubstituted $C_{3-30}$ cycloalkylene, substituted or unsubstituted $C_{3-30}$ heterocycloalkylene, substituted or unsubstituted $C_{6-30}$ arylene, substituted or unsubstituted $C_{3-30}$ heteroarylene, or a combination thereof, wherein R' may be hydrogen, substituted or unsubstituted $C_{1-20}$ alkyl, substituted or unsubstituted $C_{1-20}$ heteroalkyl, substituted or unsubstituted $C_{6-30}$ aryl, or substituted or unsubstituted $C_{3-30}$ heteroaryl.

X and one of $Y^1$ or $Y^2$ together optionally may form a ring, wherein the ring optionally further includes one or more divalent linking groups as part of its structure, wherein each of the one or more divalent linking groups is substituted or unsubstituted, and wherein the ring is substituted or unsubstituted.

In Formula (1), $Y^1$ and $Y^2$ are each independently a non-hydrogen substituent. In some aspects, $Y^1$ and $Y^2$ each independently includes an electron withdrawing group, for example a carbonyl group (—C(O)—) or a cyano group (—CN). Preferably, $Y^1$ and $Y^2$ are each independently halogen, cyano, substituted or unsubstituted $C_{1-30}$ alkyl, substituted or unsubstituted $C_{1-30}$ heteroalkyl, substituted or unsubstituted $C_{3-30}$ cycloalkyl, substituted or unsubstituted $C_{3-30}$ heterocycloalkyl, substituted or unsubstituted $C_{2-30}$ alkenyl, substituted or unsubstituted $C_{2-30}$ alkynyl, substituted or unsubstituted $C_1$-$C_{30}$ alkoxy, substituted or unsubstituted $C_1$-$C_{30}$ alkylthio, substituted or unsubstituted $C_3$-$C_{10}$ cycloalkenyl, substituted or unsubstituted $C_3$-$C_{10}$ heterocycloalkenyl, substituted or unsubstituted $C_{6-30}$ aryl, substituted or unsubstituted $C_{7-30}$ arylalkyl, substituted or unsubstituted $C_{7-30}$ alkylaryl, or substituted or unsubstituted $C_6$-$C_{30}$ aryloxy, wherein $Y^1$ and $Y^2$ each independently may optionally further include one or more divalent linking groups as part of its structure. Exemplary divalent linking groups may be selected from —O—, —C(O)—, —C(O)O—, —S—, —$S(O)_2$—, —N(R')—, —C(O)N(R')—, substituted or unsubstituted $C_{1-30}$ alkylene, substituted or unsubstituted $C_{3-10}$ cycloalkylene, substituted or unsubstituted $C_{3-10}$ heterocycloalkylene, substituted or unsubstituted $C_{6-20}$ arylene, substituted or unsubstituted $C_{3-20}$ heteroarylene, or a combination thereof, wherein R' may be hydrogen, substituted or unsubstituted $C_{1-20}$ alkyl, substituted or unsubstituted $C_{1-20}$ heteroalkyl, substituted or unsubstituted $C_{6-30}$ aryl, or substituted or unsubstituted $C_{3-30}$ heteroaryl. Typically, $Y^1$ and $Y^2$ are each independently cyano, substituted or unsubstituted $C_{1-10}$ alkyl, substituted or unsubstituted $C_{1-10}$ heteroalkyl, substituted or unsubstituted $C_{3-10}$ cycloalkyl, or substituted or unsubstituted $C_{3-10}$ heterocycloalkyl, wherein $Y^1$ and $Y^2$ each independently may optionally further include one or more divalent linking groups as part of its structure (e.g., —C(O)O—). In some aspects, $Y^1$ and/or $Y^2$ may include an acid labile group as part of its structure. For example, at least one of $Y^1$ and $Y^2$ includes an acid labile group as part of its structure.

In Formula (1), $Y^1$ and $Y^2$ together optionally may form a ring. For example, $Y^1$ and $Y^2$ together optionally may form a ring, wherein the ring optionally further includes one or more divalent linking groups as part of its structure, wherein each of the one or more divalent linking groups is substituted or unsubstituted, and wherein the ring is substituted or unsubstituted. In some aspects, $Y^1$ and $Y^2$ may be linked together via a divalent linking group that may include an acid labile group as part of its structure.

In Formula (1), $Z^2$ is hydrogen, halogen, substituted or unsubstituted $C_{1-30}$ alkyl, substituted or unsubstituted $C_{3-30}$ cycloalkyl, substituted or unsubstituted $C_{3-30}$ heterocycloalkyl, substituted or unsubstituted $C_{6-50}$ aryl, substituted or unsubstituted $C_7$-50 arylalkyl, substituted or unsubstituted $C_{7-50}$ alkylaryl, substituted or unsubstituted $C_{6-50}$ aryloxy, substituted or unsubstituted $C_{3-30}$ heteroaryl, substituted or unsubstituted $C_{4-30}$ alkylheteroaryl, substituted or unsubstituted $C_{4-30}$ heteroarylalkyl, or substituted or unsubstituted $C_{3-30}$ heteroaryloxy. Preferably, $Z^2$ may be hydrogen, halogen, substituted or unsubstituted $C_{1-10}$ alkyl, substituted or unsubstituted $C_{3-10}$ cycloalkyl, substituted or unsubstituted $C_{3-10}$ heterocycloalkyl, substituted or unsubstituted $C_{6-20}$ aryl, substituted or unsubstituted $C_{7-20}$ arylalkyl, substituted or unsubstituted $C_{7-20}$ alkylaryl, substituted or unsubstituted $C_{6-20}$ aryloxy, substituted or unsubstituted $C_{3-10}$ heteroaryl, substituted or unsubstituted $C_{4-10}$ alkylheteroaryl, substituted or unsubstituted $C_{4-10}$ heteroarylalkyl, or substituted or unsubstituted $C_{3-10}$ heteroaryloxy. Typically, $Z^2$ may be substituted or unsubstituted $C_{1-10}$ alkyl, substituted or unsubstituted $C_{3-10}$ cycloalkyl, substituted or unsubstituted $C_{3-10}$ heterocycloalkyl, substituted or unsubstituted $C_{6-20}$ aryl, substituted or unsubstituted $C_{7-20}$ arylalkyl, substituted or unsubstituted $C_{7-20}$ alkylaryl, substituted or unsubstituted $C_{6-20}$ aryloxy, substituted or unsubstituted $C_{3-10}$ heteroaryl, substituted or unsubstituted $C_{4-10}$ alkylheteroaryl, substituted or unsubstituted $C_{4-10}$ heteroarylalkyl, or substituted or unsubstituted $C_{3-10}$ heteroaryloxy.

In Formula (1), $Z^2$ optionally further comprises one or more divalent linking groups as part of its structure. Exemplary divalent linking groups may be selected from —O—, —C(O)—, —C(O)O—, —S—, —$S(O)_2$—, —N(R')—, —C(O)N(R')—, substituted or unsubstituted $C_{1-30}$ alkylene, substituted or unsubstituted $C_{3-30}$ cycloalkylene, substituted or unsubstituted $C_{3-30}$ heterocycloalkylene, substituted or unsubstituted $C_{6-30}$ arylene, substituted or unsubstituted $C_{3-30}$ heteroarylene, or a combination thereof, wherein R' may be hydrogen, substituted or unsubstituted $C_{1-20}$ alkyl, substituted or unsubstituted $C_{1-20}$ heteroalkyl, substituted or unsubstituted $C_{6-30}$ aryl, or substituted or unsubstituted $C_{3-30}$ heteroaryl.

In Formula (1), X and $Z^2$ together optionally may form a ring, wherein the ring optionally further includes one or more divalent linking groups as part of its structure, wherein each of the one or more divalent linking groups is substituted or unsubstituted, and wherein the ring is substituted or unsubstituted. Typically, X and $Z^2$ together form a ring, wherein the ring further includes one or more divalent linking groups as part of its structure, wherein each of the one or more divalent linking groups is substituted or unsubstituted, and wherein the ring is substituted or unsubstituted.

Preferably, X includes an electron withdrawing group that is directly attached or bonded to the $N^-$ in Formula (1). For example, the electron withdrawing group may be bonded to the nitrogen anion in Formula (1) (i.e., to the anionic nitrogen atom in Formula (1)).

In some aspects, X may be a moiety represented by one of Formulae (2a) to (2c):

(2a)

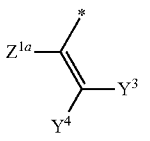

(2b)

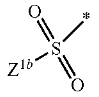

(2c)

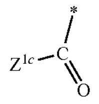

wherein * represents a point of attachment to the $N^-$ in Formula (1).

In Formula (2a), $Z^{1a}$ is hydrogen, halogen, substituted or unsubstituted $C_{1-30}$ alkyl, substituted or unsubstituted $C_{3-30}$ cycloalkyl, substituted or unsubstituted $C_{3-30}$ heterocycloalkyl, substituted or unsubstituted $C_{6-50}$ aryl, substituted or unsubstituted $C_{7-50}$ arylalkyl, substituted or unsubstituted $C_{7-50}$ alkylaryl, substituted or unsubstituted $C_{6-50}$ aryloxy, substituted or unsubstituted $C_{3-30}$ heteroaryl, substituted or unsubstituted $C_{4-30}$ alkylheteroaryl, substituted or unsubstituted $C_{4-30}$ heteroarylalkyl, or substituted or unsubstituted $C_{3-30}$ heteroaryloxy. Preferably, $Z^{1a}$ may be hydrogen, halogen, substituted or unsubstituted $C_{1-10}$ alkyl, substituted or unsubstituted $C_{3-10}$ cycloalkyl, substituted or unsubstituted $C_{3-10}$ heterocycloalkyl, substituted or unsubstituted $C_{6-20}$ aryl, substituted or unsubstituted $C_{7-20}$ arylalkyl, substituted or unsubstituted $C_{7-20}$ alkylaryl, substituted or unsubstituted $C_{6-20}$ aryloxy, substituted or unsubstituted $C_{3-10}$ heteroaryl, substituted or unsubstituted $C_{4-10}$ alkylheteroaryl, substituted or unsubstituted $C_{4-10}$ heteroarylalkyl, or substituted or unsubstituted $C_{3-10}$ heteroaryloxy. Typically, $Z^{1a}$ may be substituted or unsubstituted $C_{1-10}$ alkyl, substituted or unsubstituted $C_{3-10}$ cycloalkyl, substituted or unsubstituted $C_{3-10}$ heterocycloalkyl, substituted or unsubstituted $C_{6-20}$ aryl, substituted or unsubstituted $C_{7-20}$ arylalkyl, substituted or unsubstituted $C_{7-20}$ alkylaryl, substituted or unsubstituted $C_{6-20}$ aryloxy, substituted or unsubstituted $C_{3-10}$ heteroaryl, substituted or unsubstituted $C_{4-10}$ alkylheteroaryl, substituted or unsubstituted $C_{4-10}$ heteroarylalkyl, or substituted or unsubstituted $C_{3-10}$ heteroaryloxy.

In Formula (2a), $Z^{1a}$ optionally further comprises one or more divalent linking groups as part of its structure. Exemplary divalent linking groups may be selected from —O—, —C(O)—, —C(O)O—, —S—, —$S(O)_2$—, —N(R')—, —C(O)N(R')—, substituted or unsubstituted $C_{1-30}$ alkylene, substituted or unsubstituted $C_{3-30}$ cycloalkylene, substituted or unsubstituted $C_{3-30}$ heterocycloalkylene, substituted or unsubstituted $C_{6-30}$ arylene, substituted or unsubstituted $C_{3-30}$ heteroarylene, or a combination thereof, wherein R' may be hydrogen, substituted or unsubstituted $C_{1-20}$ alkyl, substituted or unsubstituted $C_{1-20}$ heteroalkyl, substituted or unsubstituted $C_{6-30}$ aryl, or substituted or unsubstituted $C_{3-30}$ heteroaryl.

In Formula (2a), $Y^3$ and $Y^4$ are each independently a non-hydrogen substituent. Preferably, $Y^3$ and $Y^4$ are each independently halogen, cyano, substituted or unsubstituted $C_{1-30}$ alkyl, substituted or unsubstituted $C_{1-30}$ heteroalkyl, substituted or unsubstituted $C_{3-30}$ cycloalkyl, substituted or unsubstituted $C_{3-30}$ heterocycloalkyl, substituted or unsubstituted $C_{2-30}$ alkenyl, substituted or unsubstituted $C_{2-30}$ alkynyl, substituted or unsubstituted $C_1$-$C_{30}$ alkoxy, substituted or unsubstituted $C_1$-$C_{30}$ alkylthio, substituted or unsubstituted $C_3$-$C_{10}$ cycloalkenyl, substituted or unsubstituted $C_3$-$C_{10}$ heterocycloalkenyl, substituted or unsubstituted $C_{6-30}$ aryl, substituted or unsubstituted $C_{7-30}$ arylalkyl, substituted or unsubstituted $C_{7-30}$ alkylaryl, or substituted or unsubstituted $C_6$-$C_{30}$ aryloxy, wherein $Y^3$ and $Y^4$ each independently may optionally further include one or more divalent linking groups as part of its structure. Exemplary divalent linking groups may be selected from —O—, —C(O)—, —C(O)O—, —S—, —$S(O)_2$—, —N(R')—, —C(O)N(R')—, substituted or unsubstituted $C_{1-30}$ alkylene, substituted or unsubstituted $C_{3-10}$ cycloalkylene, substituted or unsubstituted $C_{3-10}$ heterocycloalkylene, substituted or unsubstituted $C_{6-20}$ arylene, substituted or unsubstituted $C_{3-20}$ heteroarylene, or a combination thereof, wherein R' may be hydrogen, substituted or unsubstituted $C_{1-20}$ alkyl, substituted or unsubstituted $C_{1-20}$ heteroalkyl, substituted or unsubstituted $C_{6-30}$ aryl, or substituted or unsubstituted $C_{3-30}$ heteroaryl. Typically, $Y^3$ and $Y^4$ are each independently cyano, substituted or unsubstituted $C_{1-10}$ alkyl, substituted or unsubstituted $C_{1-10}$ heteroalkyl, substituted or unsubstituted $C_{3-10}$ cycloalkyl, or substituted or unsubstituted $C_{3-10}$ heterocycloalkyl, wherein $Y^3$ and $Y^4$ each independently may optionally further include one or more divalent linking groups as part of its structure (e.g., —C(O)O—). In some aspects, $Y^3$ and/or $Y^4$ may include an acid labile group as part of its structure. For example, at least one of $Y^3$ and $Y^4$ includes an acid labile group as part of its structure.

In Formula (2a), $Y^3$ and $Y^4$ together optionally may form a ring. For example, $Y^3$ and $Y^4$ together optionally may form a ring, wherein the ring optionally further includes one or more divalent linking groups as part of its structure, wherein each of the one or more divalent linking groups is substituted or unsubstituted, and wherein the ring is substituted or unsubstituted. In some aspects, $Y^3$ and $Y^4$ may be linked together via a divalent linking group that may include an acid labile group as part of its structure.

In Formula (2a), $Z^{1a}$ and one of $Y^3$ or $Y^4$ together optionally form a ring. The ring optionally further includes one or more divalent linking groups as part of its structure, wherein each of the one or more divalent linking groups is substituted or unsubstituted, and wherein the ring is substituted or unsubstituted.

In Formulae (1) and (2a), $Z^2$ and one of $Y^3$ or $Y^4$ together optionally form a ring. The ring optionally further includes one or more divalent linking groups as part of its structure, wherein each of the one or more divalent linking groups is substituted or unsubstituted, and wherein the ring is substituted or unsubstituted.

In Formulae (1) and (2a), $Z^{1a}$ and $Z^2$ together optionally form a ring. The ring optionally further includes one or more divalent linking groups as part of its structure, wherein each of the one or more divalent linking groups is substituted or unsubstituted, and wherein the ring is substituted or unsubstituted. Typically, $Z^{1a}$ and $Z^2$ together form a ring, wherein the ring further includes one or more divalent linking groups as part of its structure, wherein each of the one or more divalent linking groups is substituted or unsubstituted, and wherein the ring is substituted or unsubstituted.

In Formulae (2b) and (2c), $Z^{1b}$ and $Z^{1c}$ are each independently substituted or unsubstituted $C_{1-30}$ alkyl, substituted or unsubstituted $C_{3-30}$ cycloalkyl, substituted or unsubstituted $C_{3-30}$ heterocycloalkyl, substituted or unsubstituted $C_{6-50}$ aryl, substituted or unsubstituted $C_{7-50}$ arylalkyl, substituted or unsubstituted $C_{7-50}$ alkylaryl, substituted or unsubstituted $C_{6-50}$ aryloxy, substituted or unsubstituted $C_{3-30}$ heteroaryl, substituted or unsubstituted $C_{4-30}$ alkylheteroaryl, substituted or unsubstituted $C_{4-30}$ heteroarylalkyl, or substituted or unsubstituted $C_{3-30}$ heteroaryloxy. Preferably, $Z^{1b}$ and $Z^{1c}$ each independently may be substituted or unsubstituted $C_{1-10}$ alkyl, substituted or unsubstituted $C_{3-10}$ cycloalkyl, substituted or unsubstituted $C_{3-10}$ heterocycloalkyl, substituted or unsubstituted $C_{6-20}$ aryl, substituted or unsubstituted $C_{7-20}$ arylalkyl, substituted or unsubstituted $C_{7-20}$ alkylaryl, substituted or unsubstituted $C_{6-20}$ aryloxy, substituted or unsubstituted $C_{3-10}$ heteroaryl, substituted or unsubstituted $C_{4-10}$ alkylheteroaryl, substituted or unsubstituted $C_{4-10}$ heteroarylalkyl, or substituted or unsubstituted $C_{3-10}$ heteroaryloxy. Typically, $Z^{1b}$ and $Z^{1c}$ each independently may be substituted or unsubstituted $C_{1-10}$ alkyl, substituted or unsubstituted $C_{3-10}$ cycloalkyl, substituted or unsubstituted $C_{3-10}$ heterocycloalkyl, substituted or unsubstituted $C_{6-20}$ aryl, substituted or unsubstituted $C_{7-20}$ arylalkyl, substituted or unsubstituted $C_{7-20}$ alkylaryl, substituted or unsubstituted $C_{6-20}$ aryloxy, substituted or unsubstituted $C_{3-10}$ heteroaryl, substituted or unsubstituted $C_{4-10}$ alkylheteroaryl, substituted or unsubstituted $C_{4-10}$ heteroarylalkyl, or substituted or unsubstituted $C_{3-10}$ heteroaryloxy.

In Formulae (2b) and (2c), $Z^{1b}$ and $Z^{1c}$ each independently optionally further comprises one or more divalent linking groups as part of its structure. Exemplary divalent linking groups may be selected from —O—, —C(O)—, —C(O)O—, —S—, —$S(O)_2$—, —N(R')—, —C(O)N(R')—, substituted or unsubstituted $C_{1-30}$ alkylene, substituted or unsubstituted $C_{3-30}$ cycloalkylene, substituted or unsubstituted $C_{3-30}$ heterocycloalkylene, substituted or unsubstituted $C_{6-30}$ arylene, substituted or unsubstituted $C_{3-30}$ heteroarylene, or a combination thereof, wherein R' may be hydrogen, substituted or unsubstituted $C_{1-20}$ alkyl, substituted or unsubstituted $C_{1-20}$ heteroalkyl, substituted or unsubstituted $C_{6-30}$ aryl, or substituted or unsubstituted $C_{3-30}$ heteroaryl.

In Formulae (1) and (2b), $Z^{1b}$ and $Z^2$ together optionally form a ring. The ring optionally further includes one or more divalent linking groups as part of its structure, wherein each of the one or more divalent linking groups is substituted or unsubstituted, and wherein the ring is substituted or unsubstituted. Typically, $Z^{1b}$ and $Z^2$ together form a ring, wherein the ring further includes one or more divalent linking groups as part of its structure, wherein each of the one or more divalent linking groups is substituted or unsubstituted, and wherein the ring is substituted or unsubstituted.

In Formulae (1) and (2c), $Z^{1c}$ and $Z^2$ together optionally form a ring. The ring optionally further includes one or more divalent linking groups as part of its structure, wherein each of the one or more divalent linking groups is substituted or unsubstituted, and wherein the ring is substituted or unsubstituted. Typically, $Z^{1c}$ and $Z^2$ together form a ring, wherein the ring further includes one or more divalent linking groups as part of its structure, wherein each of the one or more divalent linking groups is substituted or unsubstituted, and wherein the ring is substituted or unsubstituted.

In some aspects, the anion represented by Formula (1) does not include and is free of —F, —$CF_3$, or —$CF_2$— groups. It should be understood that "free of —F, —$CF_3$, or —$CF_2$— groups" means that the anion of the photoacid generator excludes groups such as —$CH_2CF_3$ and —$CH_2CF_2CH_3$. In still other aspects, the anion represented by Formula (1) is free of fluorine (i.e., does not contain a fluorine atom and is not substituted by a fluorine-containing group). In some aspects, the photoactive compound is free of fluorine (i.e., both the organic cation and the anion represented by Formula (1) are free of fluorine).

For example, in Formula (1), one or more of X, $Y^1$, $Y^2$, and $Z^2$ is free of fluorine, and preferably all of X, $Y^1$, $Y^2$, and $Z^2$ are free of fluorine. For example, in Formula (1), (2a), (2b), and (2c), one or more of $Y^1$, $Y^2$, $Y^3$, $Y^4$, $Z^{1a}$, $Z^{1b}$, $Z^{1c}$, and $Z^2$ is free of fluorine, and preferably all of $Y^1$, $Y^2$, $Y^3$, $Y^4$, $Z^{1a}$, $Z^{1b}$, $Z^{1c}$, and $Z^2$ are free of fluorine.

In some aspects, as described above, the anion represented by Formula (1) may comprise one or more acid labile groups. For example, in Formula (1), one or more of X, $Y^1$, $Y^2$, and $Z^2$ comprises an acid labile group. For example, in Formula (1), (2a), (2b), and (2c), one or more of $Y^1$, $Y^2$, $Y^3$, $Y^4$, $Z^{1a}$, $Z^{1b}$, $Z^{1c}$, and $Z^2$ comprises an acid labile group.

In some aspects, the photoactive compound of Formula (1) may be represented by one or more of Formulae (3a) to (3c):

(3a)

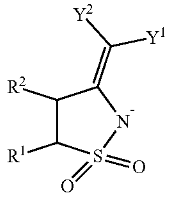

(3b)

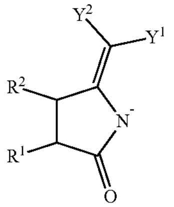

(3c)

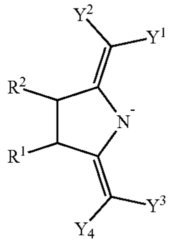

In Formulae (3a) and (3b), $Y^1$ and $Y^2$ are as defined for $Y^1$ and $Y^2$ in Formula (1). In Formula (3c), $Y^1$ and $Y^2$ are as defined for $Y^1$ and $Y^2$ in Formula (1) and $Y^3$ and $Y^4$ are as defined for $Y^3$ and $Y^4$ in Formula (2a).

In Formulae (3a) to (3c), $R^1$ and $R^2$ are each independently substituted or unsubstituted $C_{1-30}$ alkyl, substituted or unsubstituted $C_{3-30}$ cycloalkyl, substituted or unsubstituted $C_{3-30}$ heterocycloalkyl, substituted or unsubstituted $C_{6-30}$ aryl, substituted or unsubstituted $C_{7-30}$ arylalkyl, substituted or unsubstituted $C_{7-30}$ alkylaryl, substituted or unsubstituted $C_{6-30}$ aryloxy, substituted or unsubstituted $C_{3-30}$ heteroaryl, substituted or unsubstituted $C_{4-30}$ alkylheteroaryl, substituted or unsubstituted $C_{4-30}$ heteroarylalkyl, or substituted or unsubstituted $C_{3-30}$ heteroaryloxy.

In Formulae (3a) to (3c), $R^1$ and $R^2$ each independently optionally further comprises one or more divalent linking groups as part of its structure. Exemplary divalent linking groups may be selected from —O—, —C(O)—, —C(O)O—, —S—, —$S(O)_2$—, —N(R')—, —C(O)N(R')—, substituted or unsubstituted $C_{1-30}$ alkylene, substituted or unsubstituted $C_{3-30}$ cycloalkylene, substituted or unsubstituted $C_{3-30}$ heterocycloalkylene, substituted or unsubstituted $C_{6-30}$ arylene, substituted or unsubstituted $C_{3-30}$ heteroarylene, or a combination thereof, wherein R' may be hydrogen, substituted or unsubstituted $C_{1-20}$ alkyl, substituted or unsubstituted $C_{1-20}$ heteroalkyl, substituted or unsubstituted $C_{6-30}$ aryl, or substituted or unsubstituted $C_{3-30}$ heteroaryl.

In Formulae (3a) to (3c), $R^1$ and $R^2$ together optionally may form a ring, wherein the ring optionally further includes one or more divalent linking groups as part of its structure, wherein each of the one or more divalent linking groups is substituted or unsubstituted, and wherein the ring is substituted or unsubstituted. Typically, $R^1$ and $R^2$ together form a ring, wherein the ring further includes one or more divalent linking groups as part of its structure, wherein each of the one or more divalent linking groups is substituted or unsubstituted, and wherein the ring is substituted or unsubstituted.

The anion represented by Formulae (3a) to (3c) may be free of fluorine. For example, in Formulae (3a) and (3b), one or more of $R^1$, $R^2$, $Y^1$, and $Y^2$ is free of fluorine, and preferably all of $R^1$, $R^2$, $Y^1$, and $Y^2$ are free of fluorine. For example, in Formula (3c), one or more of $R^1$, $R^2$, $Y^1$, $Y^2$, $Y^3$, and $Y^4$ is free of fluorine, and preferably all of $R^1$, $R^2$, $Y^1$, $Y^2$, $Y^3$, and $Y^4$ are free of fluorine.

The anion represented by Formulae (3a) to (3c) may comprise one or more acid labile groups. For example, in Formulae (3a) and (3b), one or more of $R^1$, $R^2$, $Y^1$, and $Y^2$ comprises an acid labile group. For example, in Formula (3c), one or more of $R^1$, $R^2$, $Y^1$, $Y^2$, $Y^3$, and $Y^4$ comprises an acid labile group.

In some aspects, the photoactive compound of Formula (1) may be represented by one or more of Formulae (4a) to (4c):

(4a)

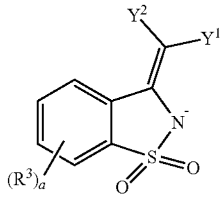

(4b)

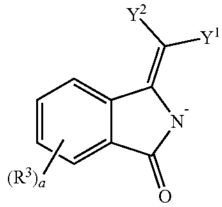

(4c)

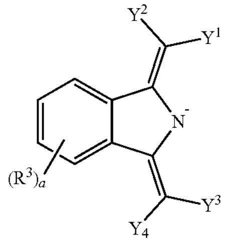

In Formulae (4a) and (4b), $Y^1$ and $Y^2$ are as defined for $Y^1$ and $Y^2$ in Formula (1). In Formula (4c), $Y^1$ and $Y^2$ are as defined for $Y^1$ and $Y^2$ in Formula (1) and $Y^3$ and $Y^4$ are as defined for $Y^3$ and $Y^4$ in Formula (2a).

In Formulae (4a) to (4c), each $R^3$ is independently halogen, cyano, substituted or unsubstituted $C_{1-30}$ alkyl, substituted or unsubstituted $C_{3-30}$ cycloalkyl, substituted or unsubstituted $C_{3-30}$ heterocycloalkyl, substituted or unsubstituted $C_{6-30}$ aryl, substituted or unsubstituted $C_{7-30}$ arylalkyl, substituted or unsubstituted $C_{7-30}$ alkylaryl, substituted or unsubstituted $C_{6-30}$ aryloxy, substituted or unsubstituted $C_{3-30}$ heteroaryl, substituted or unsubstituted $C_{4-30}$ alkylheteroaryl, substituted or unsubstituted $C_{4-30}$ heteroarylalkyl, or substituted or unsubstituted $C_{3-30}$ heteroaryloxy.

In Formulae (4a) to (4c), each $R^3$ independently optionally further comprises one or more divalent linking groups as part of its structure. Exemplary divalent linking groups may be selected from —O—, —C(O)—, —C(O)O—, —S—, —$S(O)_2$—, —N(R')—, —C(O)N(R')—, substituted or unsubstituted $C_{1-30}$ alkylene, substituted or unsubstituted $C_{3-30}$ cycloalkylene, substituted or unsubstituted $C_{3-30}$ heterocycloalkylene, substituted or unsubstituted $C_{6-30}$ arylene, substituted or unsubstituted $C_{3-30}$ heteroarylene, or a combination thereof, wherein R' may be hydrogen, substituted or unsubstituted $C_{1-20}$ alkyl, substituted or unsubstituted $C_{1-20}$ heteroalkyl, substituted or unsubstituted $C_{6-30}$ aryl, or substituted or unsubstituted $C_{3-30}$ heteroaryl.

In Formulae (4a) to (4c), a is an integer from 0 to 4, preferably from 0 to 2, and typically 0 or 1.

In Formulae (4a) to (4c), when a is 2 or greater, adjacent two or more of $R^3$ together optionally may form a ring, wherein the ring optionally further includes one or more divalent linking groups as part of its structure, wherein each of the one or more divalent linking groups is substituted or unsubstituted, and wherein the ring is substituted or unsubstituted.

The anion represented by Formulae (4a) to (4c) may be free of fluorine. For example, in Formulae (4a) and (4b), one or more of $R^3$, $Y^1$, and $Y^2$ is free of fluorine, and preferably all of $R^3$, $Y^1$, and $Y^2$ are free of fluorine. For example, in Formula (4c), one or more of $R^3$, $Y^1$, $Y^2$, $Y^3$, and $Y^4$ is free of fluorine, and preferably all of $R^3$, $Y^1$, $Y^2$, $Y^3$, and $Y^4$ are free of fluorine.

The anion represented by Formulae (4a) to (4c) may comprise one or more acid labile groups. For example, in Formulae (4a) and (4b), one or more of $R^3$, $Y^1$, and $Y^2$ comprises an acid labile group. For example, in Formula (4c), one or more of $R^3$, $Y^1$, $Y^2$, $Y^3$, and $Y^4$ comprises an acid labile group.

In some aspects, the photoactive compound of Formula (1) may be represented by one or more of Formulae (5a) to (5c):

(5a)

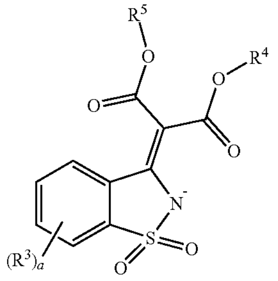

(5b)

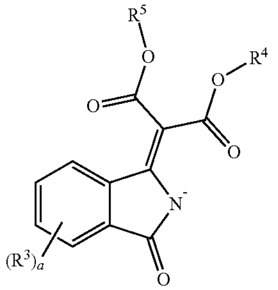

-continued (5c)

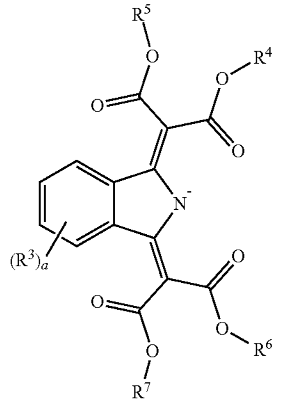

In Formulae (5a) to (5c), $R^3$ and a are each as defined for $R^3$ and a in Formulae (4a) to (4c).

In Formulae (5a) and (5b), $R^4$ and $R^5$ are each independently hydrogen, substituted or unsubstituted $C_{1-30}$ alkyl, substituted or unsubstituted $C_{3-30}$ cycloalkyl, substituted or unsubstituted $C_{3-30}$ heterocycloalkyl, substituted or unsubstituted $C_{6-30}$ aryl, substituted or unsubstituted $C_{7-30}$ arylalkyl, substituted or unsubstituted $C_{7-30}$ alkylaryl, substituted or unsubstituted $C_{6-30}$ aryloxy, substituted or unsubstituted $C_{3-30}$ heteroaryl, substituted or unsubstituted $C_{4-30}$ alkylheteroaryl, substituted or unsubstituted $C_{4-30}$ heteroarylalkyl, or substituted or unsubstituted $C_{3-30}$ heteroaryloxy.

In Formulae (5a) and (5b), $R^4$ and $R^5$ each independently optionally further comprises one or more divalent linking groups as part of its structure. Exemplary divalent linking groups may be selected from —O—, —C(O)—, —C(O)O—, —S—, —S(O)$_2$—, —N(R')—, —C(O)N(R')—, substituted or unsubstituted $C_{1-30}$ alkylene, substituted or unsubstituted $C_{3-30}$ cycloalkylene, substituted or unsubstituted $C_{3-30}$ heterocycloalkylene, substituted or unsubstituted $C_{6-30}$ arylene, substituted or unsubstituted $C_{3-30}$ heteroarylene, or a combination thereof, wherein R' may be hydrogen, substituted or unsubstituted $C_{1-20}$ alkyl, substituted or unsubstituted $C_{1-20}$ heteroalkyl, substituted or unsubstituted $C_{6-30}$ aryl, or substituted or unsubstituted $C_{3-30}$ heteroaryl.

In Formulae (5a) and (5b), $R^4$ and $R^5$ together optionally may form a ring, wherein the ring optionally further includes one or more divalent linking groups as part of its structure, wherein each of the one or more divalent linking groups is substituted or unsubstituted, and wherein the ring is substituted or unsubstituted.

In Formula (5c), $R^4$ to $R^7$ are each independently hydrogen, substituted or unsubstituted $C_{1-30}$ alkyl, substituted or unsubstituted $C_{3-30}$ cycloalkyl, substituted or unsubstituted $C_{3-30}$ heterocycloalkyl, substituted or unsubstituted $C_{6-30}$ aryl, substituted or unsubstituted $C_{7-30}$ arylalkyl, substituted or unsubstituted $C_{7-30}$ alkylaryl, substituted or unsubstituted $C_{6-30}$ aryloxy, substituted or unsubstituted $C_{3-30}$ heteroaryl, substituted or unsubstituted $C_{4-30}$ alkylheteroaryl, substituted or unsubstituted $C_{4-30}$ heteroarylalkyl, or substituted or unsubstituted $C_{3-30}$ heteroaryloxy.

In Formula (5c), $R^4$ to $R^7$ each independently optionally further comprises one or more divalent linking groups as part of its structure. Exemplary divalent linking groups may be selected from —O—, —C(O)—, —C(O)O—, —S—, —S(O)$_2$—, —N(R')—, —C(O)N(R')—, substituted or unsubstituted $C_{1-30}$ alkylene, substituted or unsubstituted $C_{3-30}$ cycloalkylene, substituted or unsubstituted $C_{3-30}$ heterocycloalkylene, substituted or unsubstituted $C_{6-30}$ arylene, substituted or unsubstituted $C_{3-30}$ heteroarylene, or a combination thereof, wherein R' may be hydrogen, substituted or unsubstituted $C_{1-20}$ alkyl, substituted or unsubstituted $C_{1-20}$ heteroalkyl, substituted or unsubstituted $C_{6-30}$ aryl, or substituted or unsubstituted $C_{3-30}$ heteroaryl.

In Formula (5c), $R^4$ and $R^5$ together optionally may form a ring, wherein the ring optionally further includes one or more divalent linking groups as part of its structure, wherein each of the one or more divalent linking groups is substituted or unsubstituted, and wherein the ring is substituted or unsubstituted; and/or $R^6$ and $R^7$ together optionally may form a ring, wherein the ring optionally further includes one or more divalent linking groups as part of its structure, wherein each of the one or more divalent linking groups is substituted or unsubstituted, and wherein the ring is substituted or unsubstituted.

The anion represented by Formulae (5a) to (5c) may be free of fluorine. For example, in Formulae (5a) and (5b), one or more of $R^3$, $R^4$, and $R^5$ is free of fluorine, and preferably all of $R^3$, $R^4$, and $R^5$ are free of fluorine. For example, in Formula (5c), one or more of $R^3$ to $R^7$ is free of fluorine, and preferably all of $R^3$ to $R^7$ are free of fluorine.

The anion represented by Formulae (5a) to (5c) may comprise one or more acid labile groups. For example, in Formulae (5a) and (5b), one or more of $R^3$, $R^4$, and $R^5$ comprises an acid labile group. For example, in Formula (5c), one or more of $R^3$ to $R^7$ comprises an acid labile group.

In some aspects, the photoactive compound of Formula (1) may be represented by one or more of Formulae (6a) to (6c):

(6a)

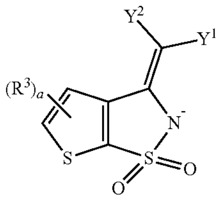

(6b)

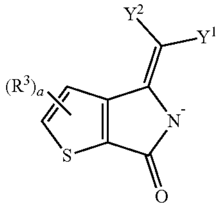

(6c)

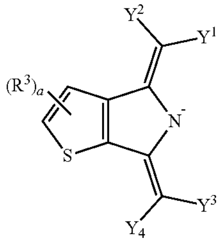

wherein $Y^1$ and $Y^2$ are as defined for Y and Y in Formula (1), $Y^3$ and $Y^4$ are as defined for $Y^3$ and $Y^4$ in Formula (2a), and $R^3$ and a are as defined for $R^3$ and a in Formulae (4a) to (4c).

Exemplary anions represented by Formula (1) include the following:

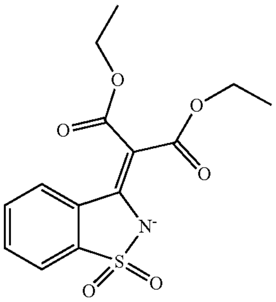
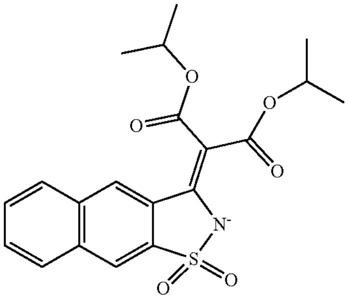
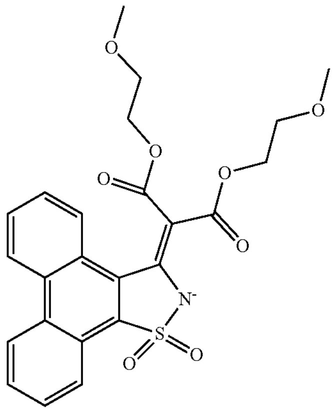
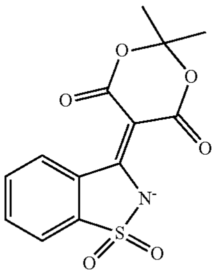
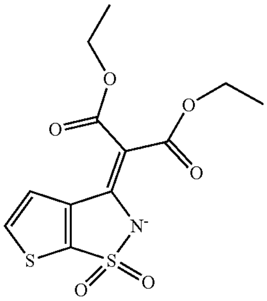
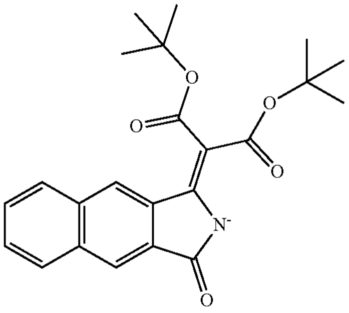
-continued
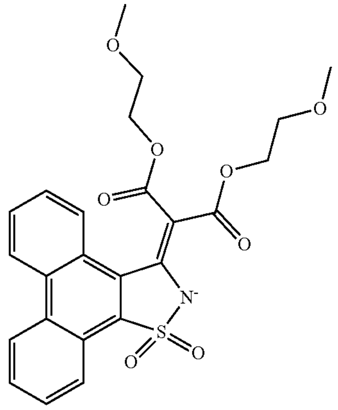
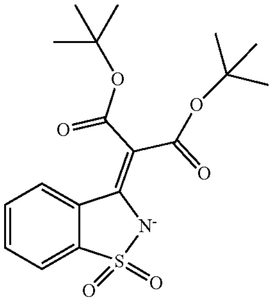
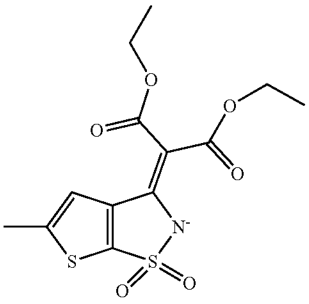
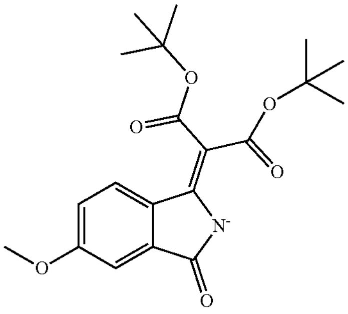
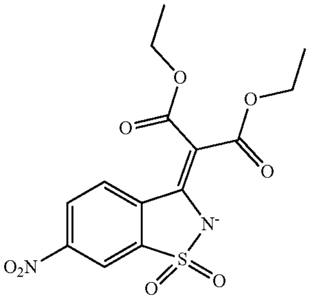

-continued
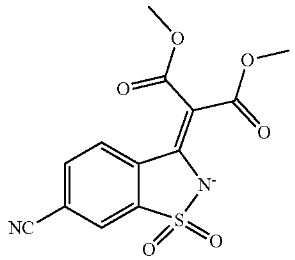
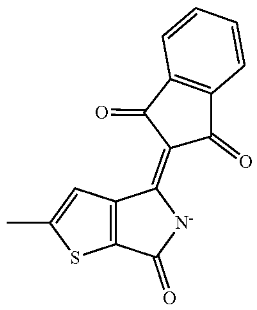
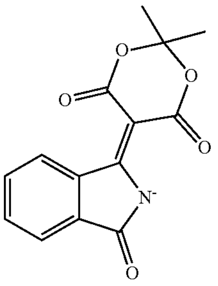
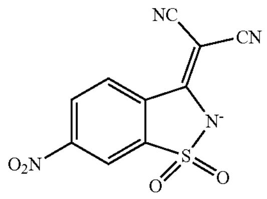
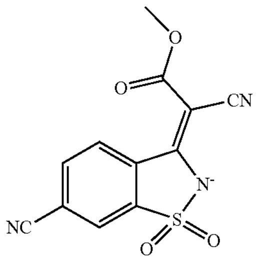
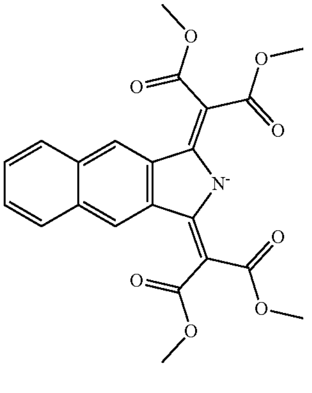
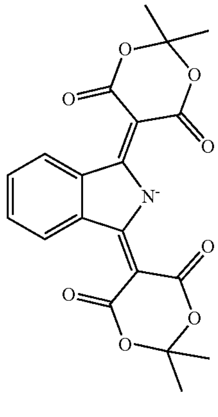
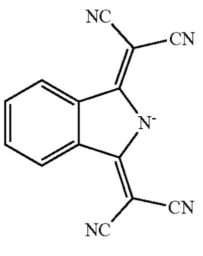
-continued
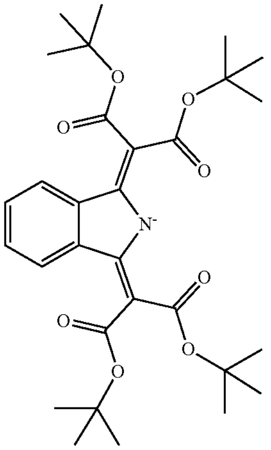
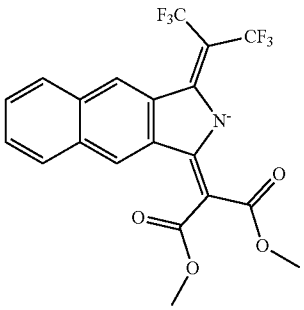
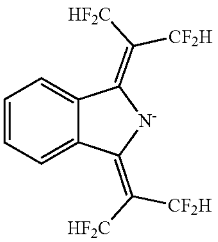
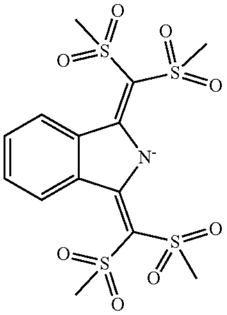
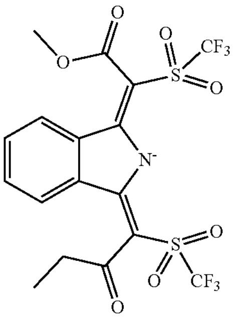
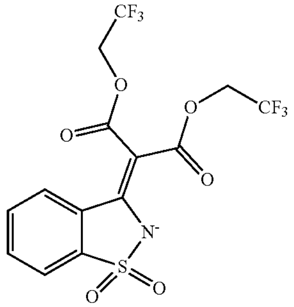
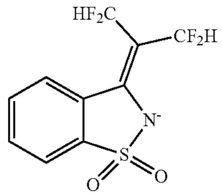
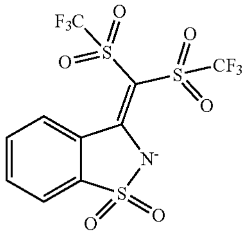
The photoactive compound also includes an organic cation. For example, the organic cation may be a sulfonium cation or an iodonium cation. In some embodiments, the organic cations may be a sulfonium cation of Formula (7a) or an iodonium cation of Formula (7b):
(7a)
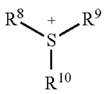

-continued

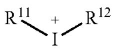

(7b)

In Formulae (7a) and (7b), $R^8$ to $R^{12}$ are each independently substituted or unsubstituted $C_{1-20}$ alkyl, substituted or unsubstituted $C_{3-20}$ cycloalkyl, substituted or unsubstituted $C_{2-20}$ alkenyl, substituted or unsubstituted $C_{6-30}$ aryl, substituted or unsubstituted $C_{6-30}$ iodoaryl, substituted or unsubstituted $C_{3-30}$ heteroaryl, substituted or unsubstituted $C_{7-20}$ arylalkyl, or substituted or unsubstituted $C_{4-20}$ heteroarylalkyl, or combinations thereof. Each of $R^8$ to $R^{10}$ may be either separate or connected to another group of $R^8$ to $R^{10}$ via a single bond or a divalent linking group to form a ring. $R^{11}$ and $R^{12}$ may be either separate or connected to each other via a single bond or a divalent linking group to form a ring. Each of $R^8$ to $R^{12}$ optionally may include as part of its structure a divalent linking group. Each of $R^8$ to $R^{12}$ independently may optionally comprise an acid-labile group chosen, for example, from tertiary alkyl ester groups, secondary or tertiary aryl ester groups, secondary or tertiary ester groups having a combination of alkyl and aryl groups, tertiary alkoxy groups, acetal groups, or ketal groups.

Exemplary sulfonium cations of Formula (7a) include one or more of the following:

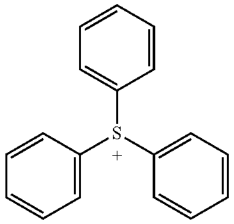

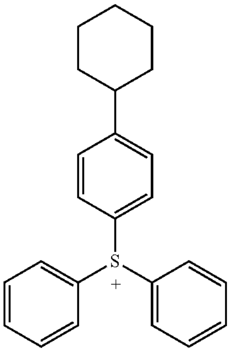

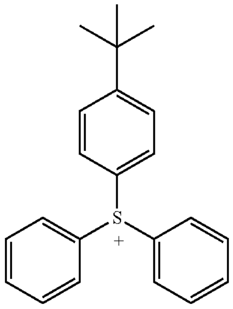

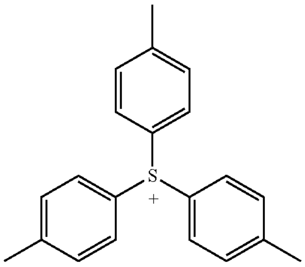

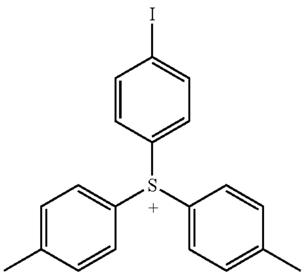

-continued

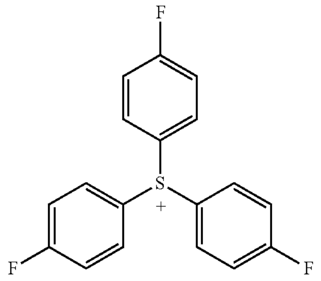

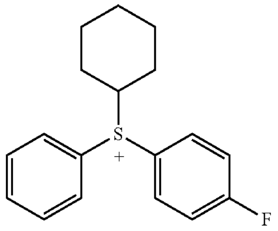

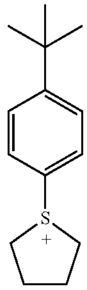

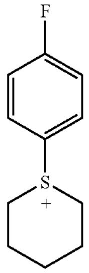

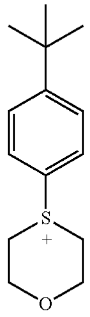

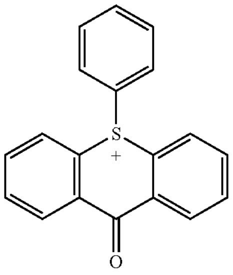

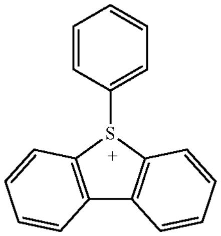

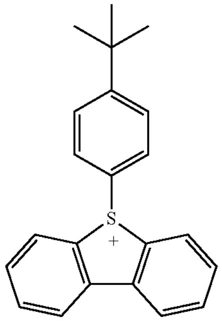

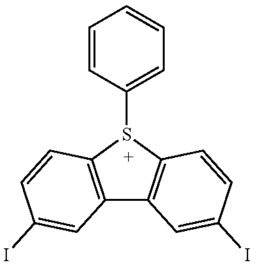

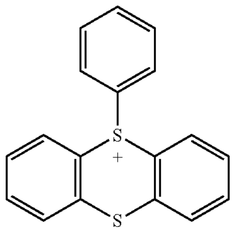

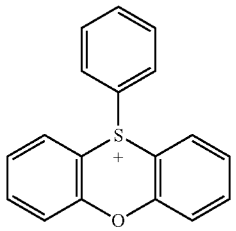

-continued
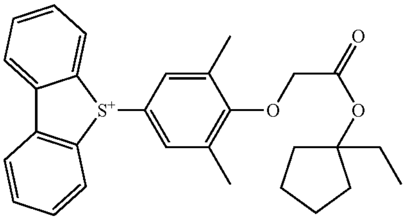
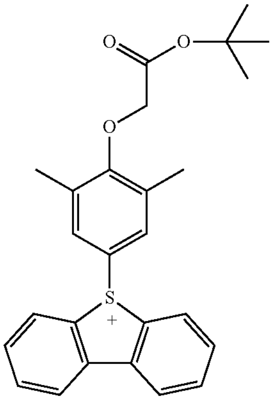
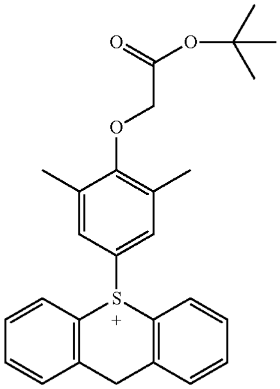
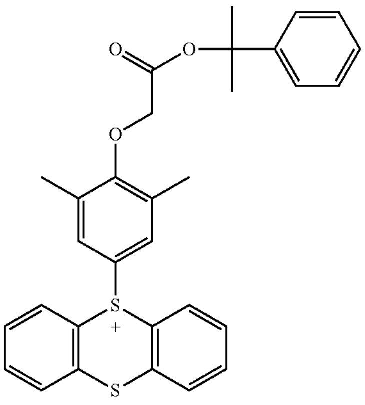
-continued
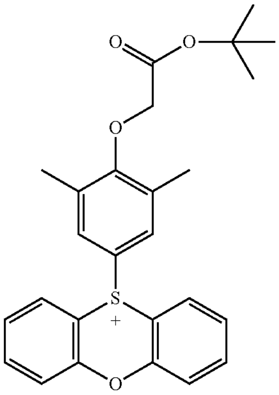
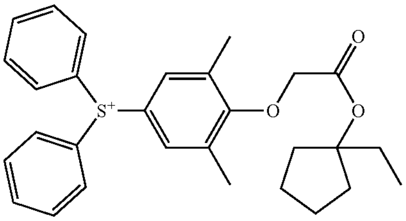
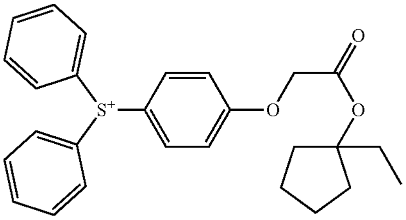
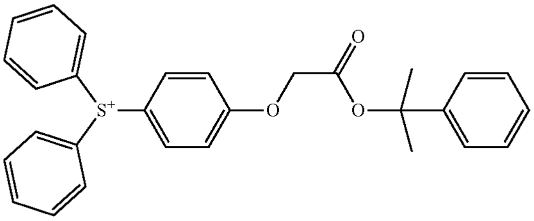
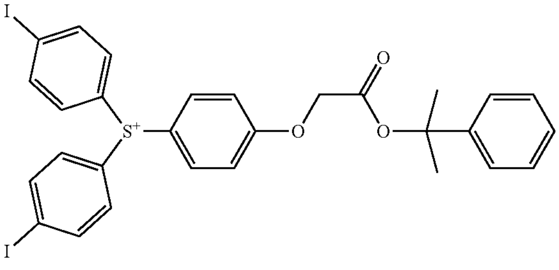

-continued
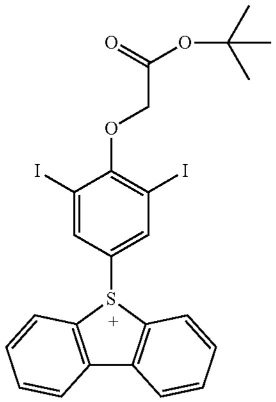
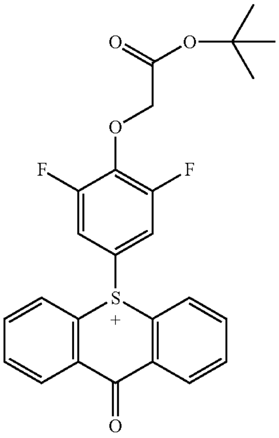
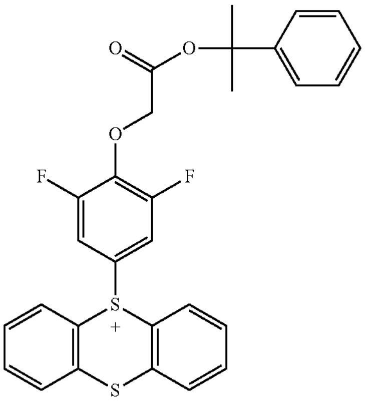
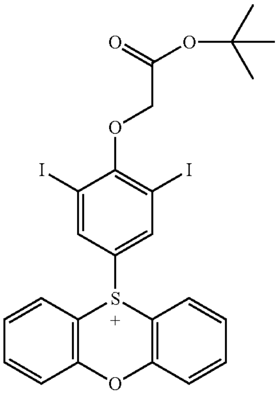
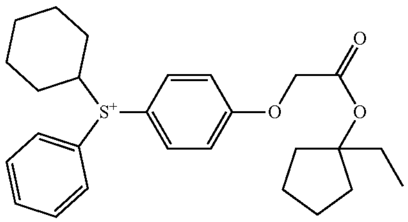 [SMILES: CCC1(OC(=O)COc2ccc([S+](c3ccccc3)C3CCCCC3)cc2)CCCC1]
Exemplary iodonium cations of Formula (7b) may include one or more of the following:
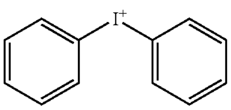
-continued
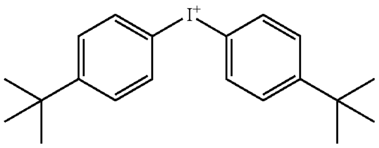
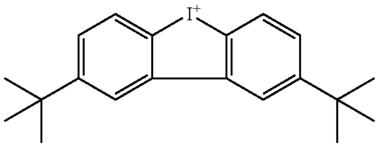
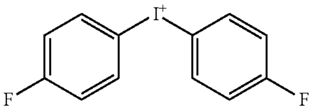
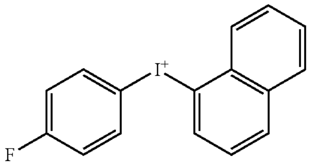
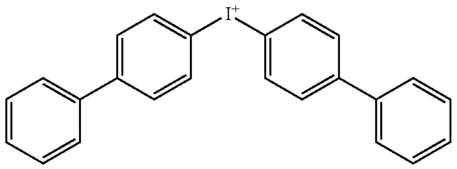
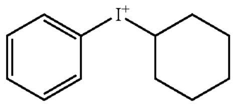
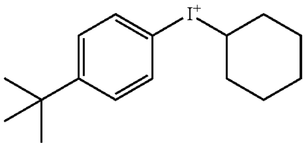
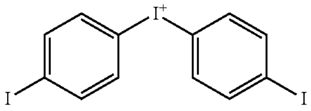
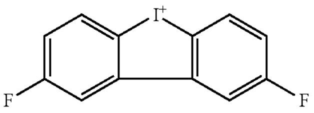
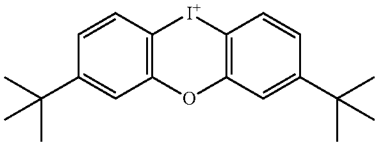
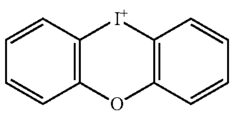
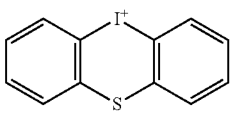
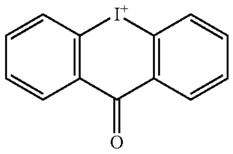
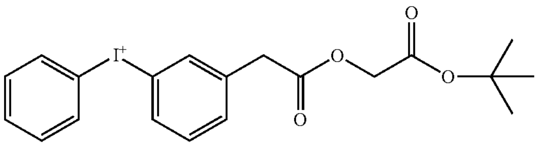

-continued

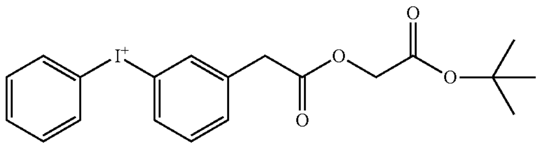

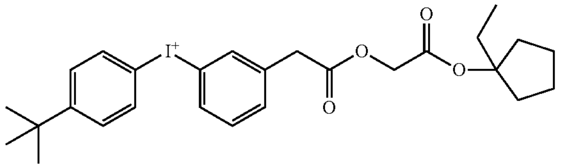

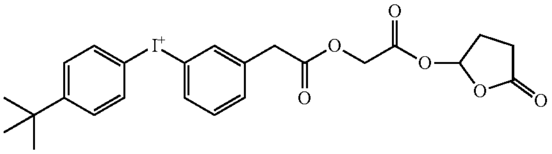

The photoactive compound may be prepared using any suitable methods in the art, including those described herein in the examples.

The present invention further relates to photoresist compositions that include the photoactive compound and a polymer, and may contain additional, optional components. Typically, the photoresist composition will further include one or more solvents, a photoacid generator (PAG), or a combination thereof.

The polymer may include one or more repeating units. The repeating units may be, for example, one or more units for purposes of adjusting properties of the photoresist composition, such as etch rate and solubility. Exemplary repeating units may include those derived from one or more of (meth)acrylate, vinyl aromatic, vinyl ether, vinyl ketone, and/or vinyl ester monomers. The polymer of the photoresist composition may be a homopolymer or a copolymer that includes two or more structurally different repeating units. For example, the polymer may include one or more repeating units that include a functional group selected from a hydroxyaryl group, an acid-labile group, a base-solubilizing group, a lactone-containing group, a sultone-containing group, a polar group, a crosslinkable group, a crosslinking group, or the like, or a combination thereof.

In one or more embodiments, the polymer may include a repeating unit formed from a monomer that includes an acid-labile group. Suitable acid-labile group include, for example, tertiary ester, acetal, ketal, and tertiary ether groups.

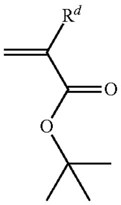 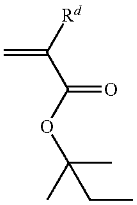 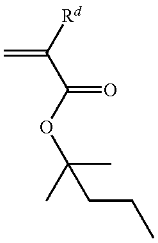

-continued

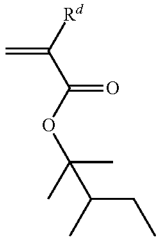 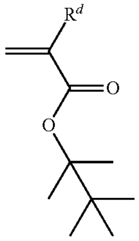 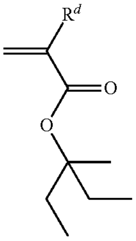

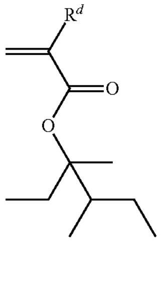 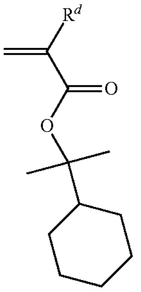 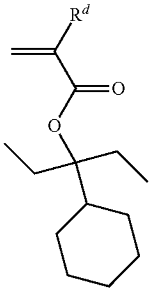

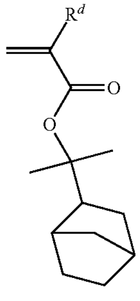 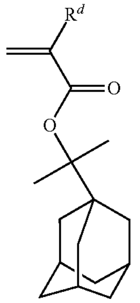 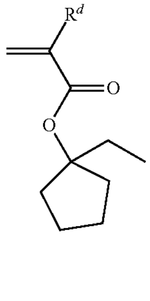

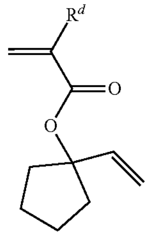 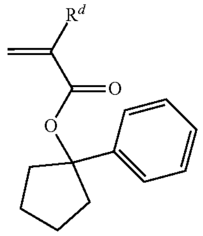 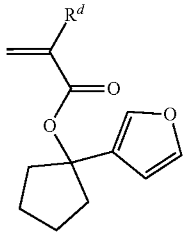

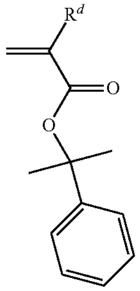 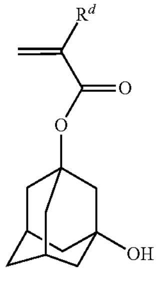 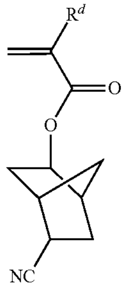

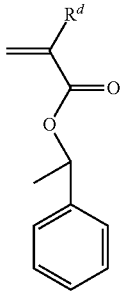 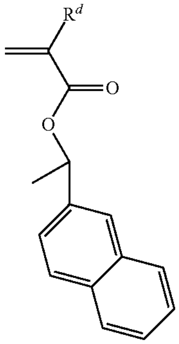 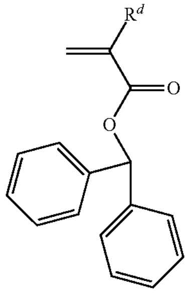

-continued
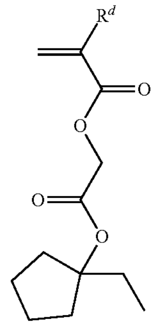
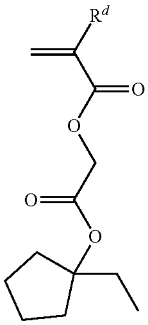
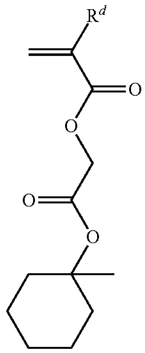
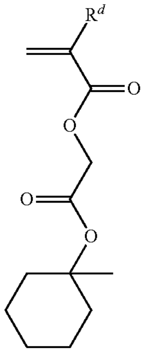
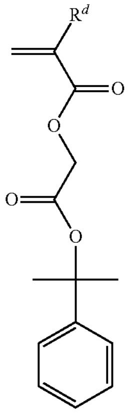
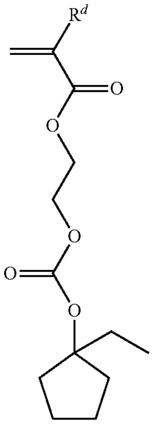
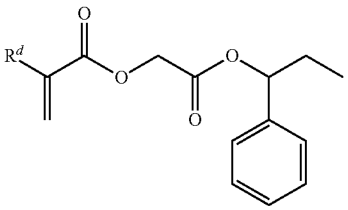
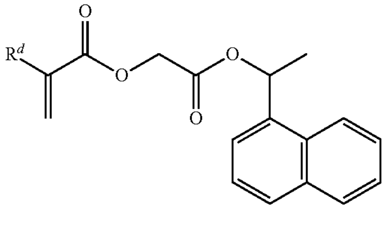
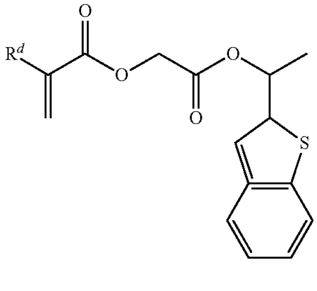
-continued
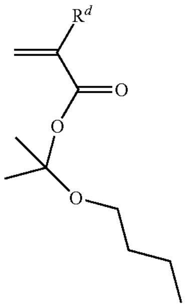
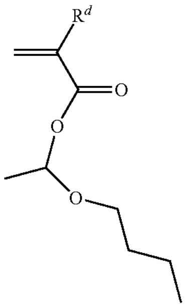
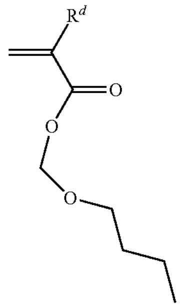
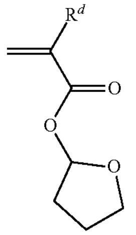
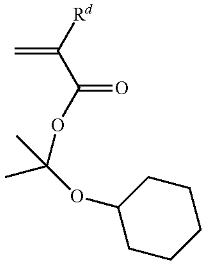
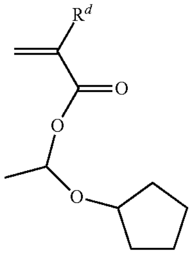
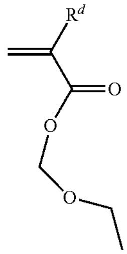
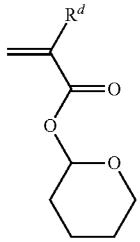
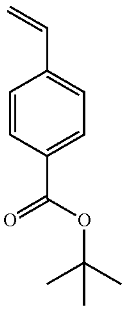
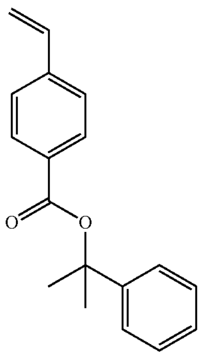
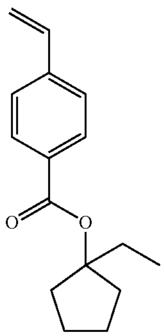
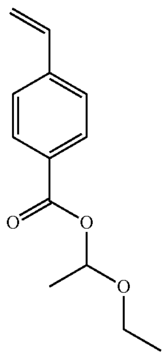
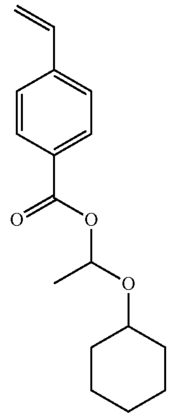

wherein $R^d$ is hydrogen, halogen, substituted or unsubstituted $C_{1-6}$ alkyl, or substituted or unsubstituted $C_{3-6}$ cycloalkyl.

When a repeating unit having an acid-labile group is present in the polymer, it is typically present in an amount from 25 to 75 mol %, more typically from 25 to 50 mol %, still more typically from 30 to 50 mol %, based on total repeating units in the polymer.

In some embodiments, the polymer may include repeating unit derived from one or more lactone-containing monomers. Suitable lactone-containing monomers include, for example, one or more of the following:

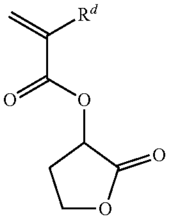
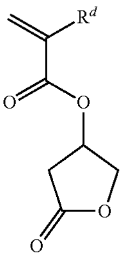
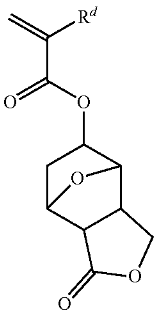
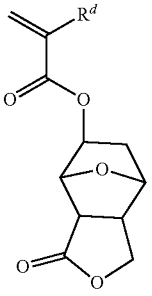
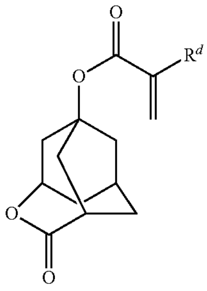
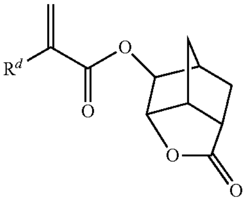
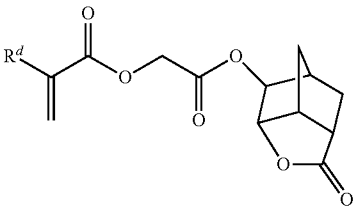
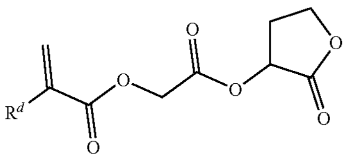

-continued

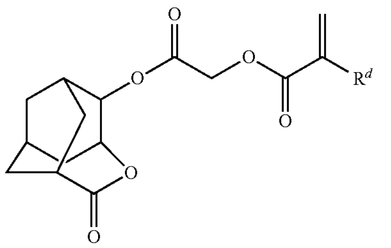

wherein $R^d$ is hydrogen, halogen, substituted or unsubstituted $C_{1-6}$ alkyl, or substituted or unsubstituted $C_{3-6}$ cycloalkyl.

In some embodiments, the polymer may include a repeating unit having a base-solubilizing group and/or having a pKa of less than or equal to 12. Exemplary base-solubilizing groups may comprise a fluoroalcohol group, a carboxylic acid group, a carboximide group, a sulfonamide group, or a sulfonimide group.

Non-limiting examples of monomers including a base-solubilizing include one or more of the following:

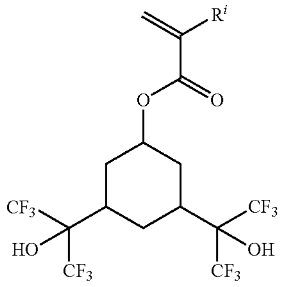
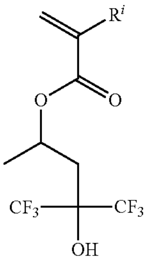
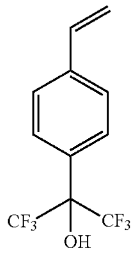
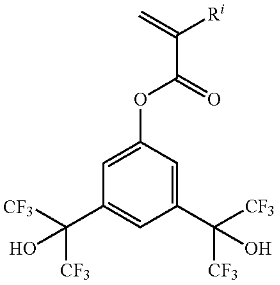
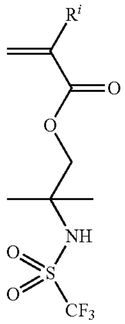
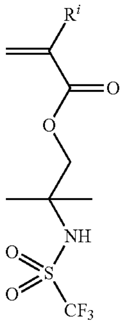
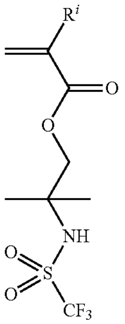
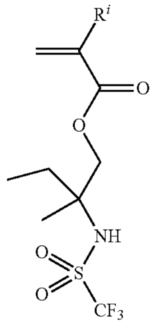

-continued
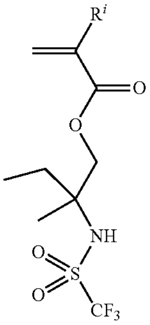
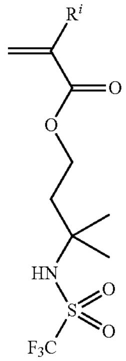
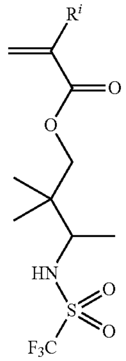
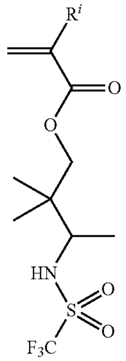
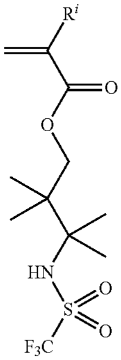
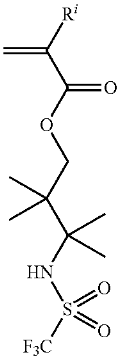
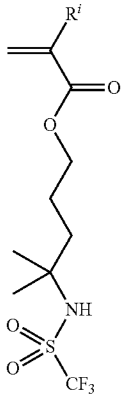
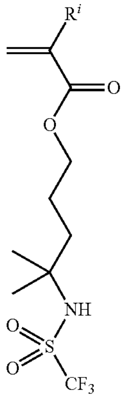
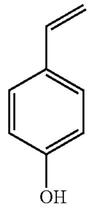
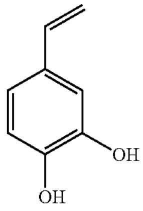
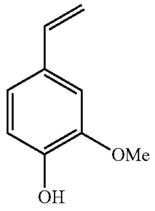
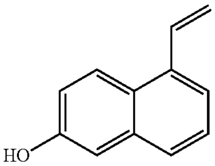
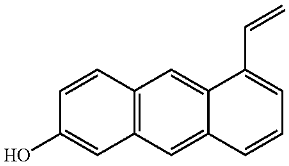
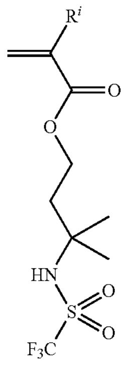
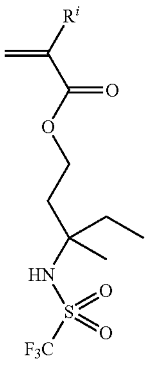
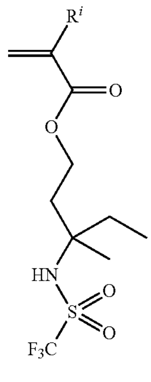
-continued
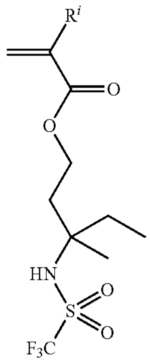
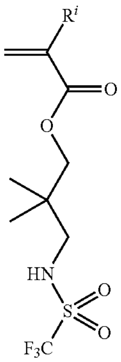
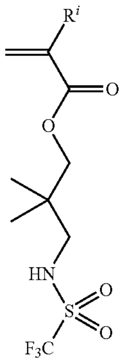
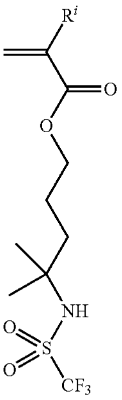
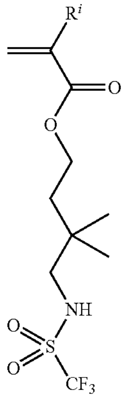
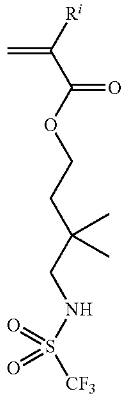
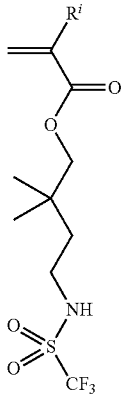
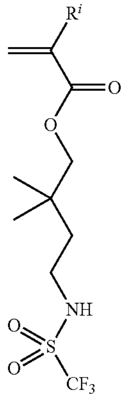
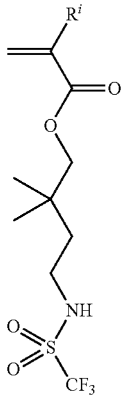
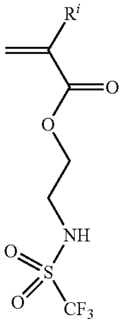
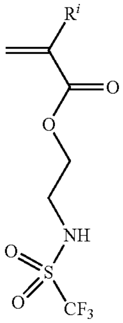
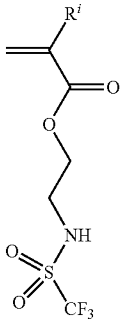
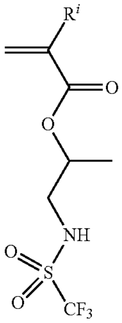
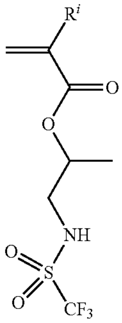
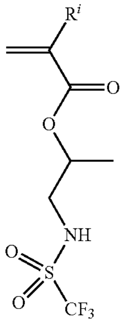

-continued

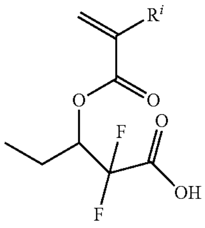

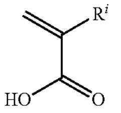

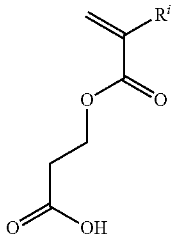

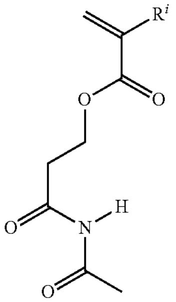

wherein each $R^i$ is independently hydrogen, halogen, substituted or unsubstituted $C_{1-6}$ alkyl, or substituted or unsubstituted $C_{3-6}$ cycloalkyl.

The polymer may further optionally include one or more additional repeating units. The additional repeating units may be, for example, one or more additional units for purposes of adjusting properties of the photoresist composition, such as etch rate and solubility. Exemplary additional units may include those derived from one or more of (meth)acrylate, vinyl aromatic, vinyl ether, vinyl ketone, and/or vinyl ester monomers. The one or more additional repeating units, if present in the first and/or second polymer, may be used in an amount of up to 50 mol %, typically from 3 to 50 mol %, based on total repeating units of the polymer.

Non-limiting exemplary polymers of the present invention include one or more of the following:

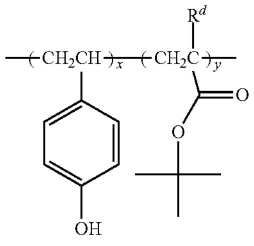

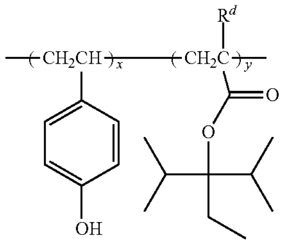

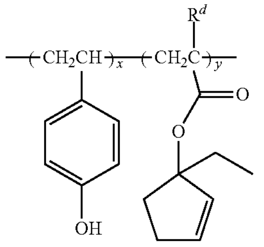

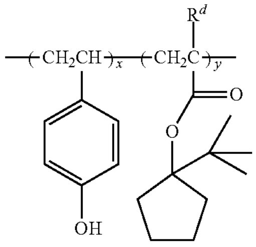

-continued

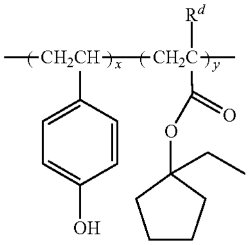

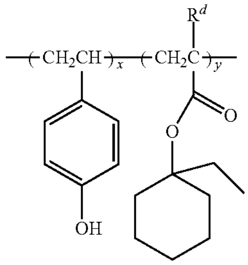

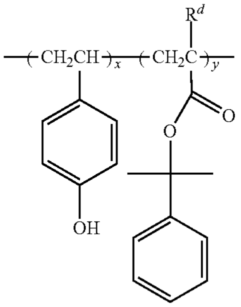

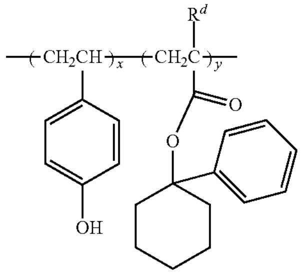

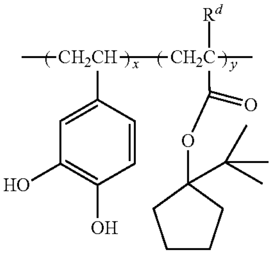

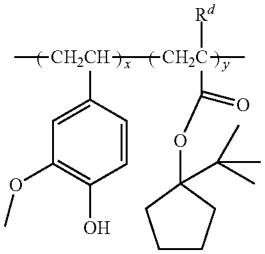

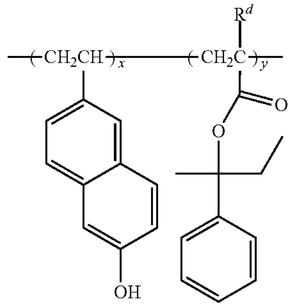

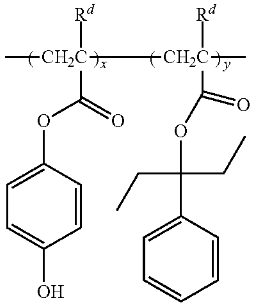

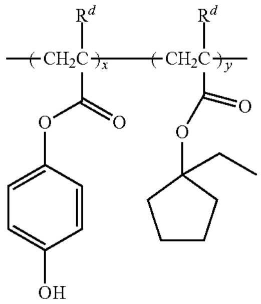

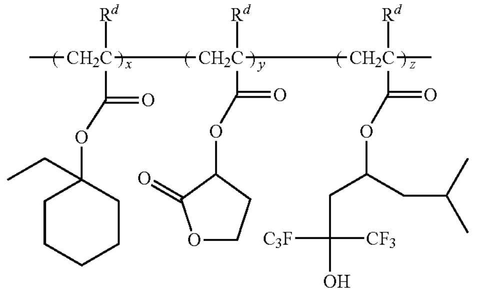

-continued
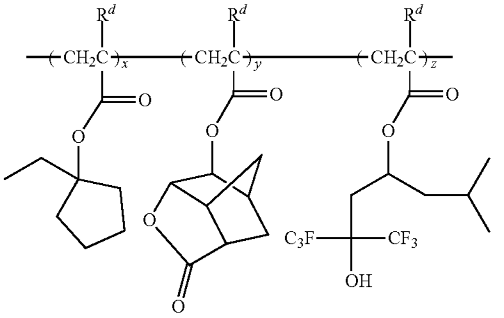
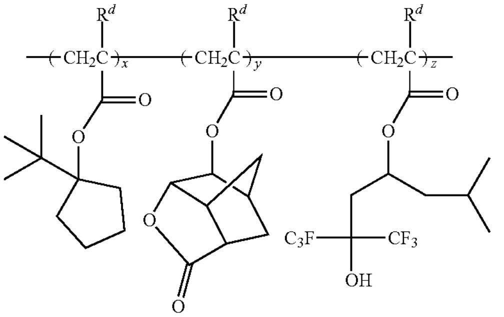
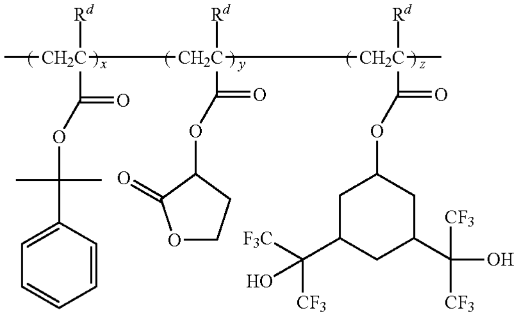
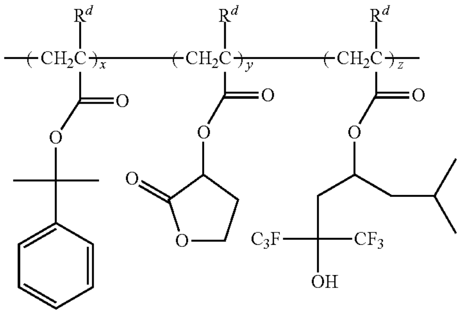
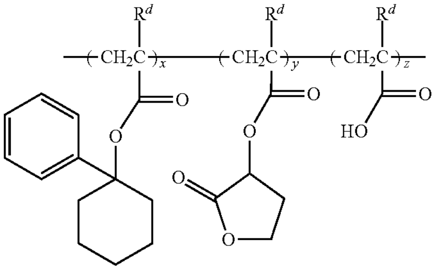
-continued
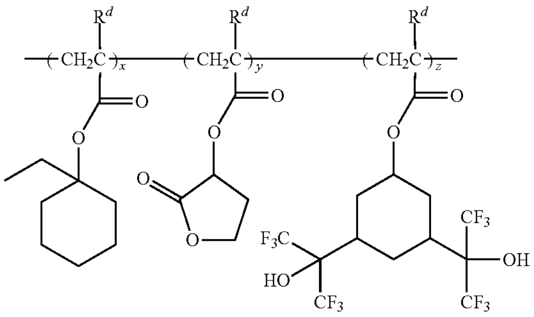
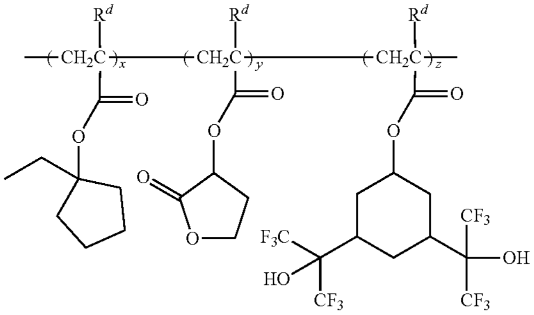
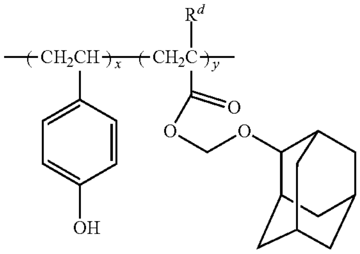
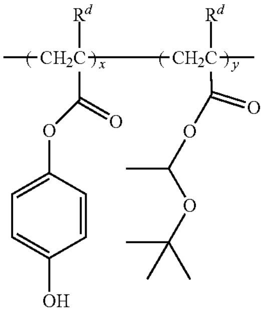
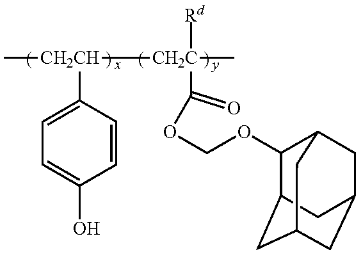

-continued

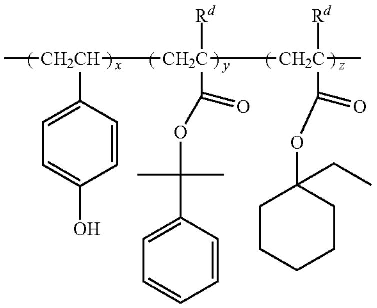

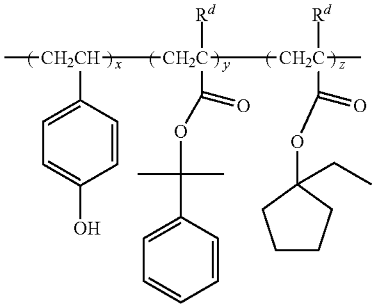

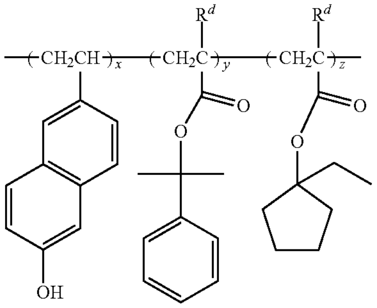

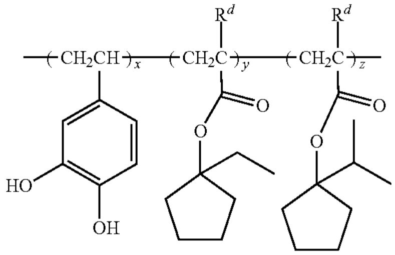

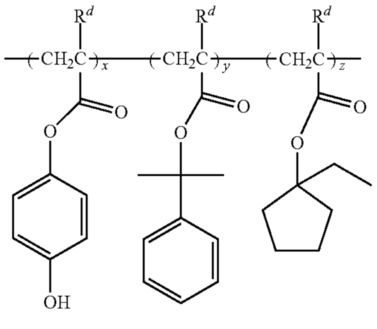

-continued

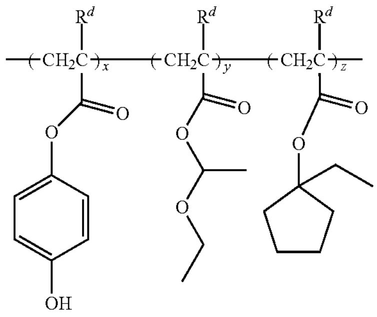

wherein each of x, y and z is a molar fraction of an associate repeating unit, wherein the sum of the molar fractions for each polymer adds up to 1, and wherein each $R^d$ is independently hydrogen, halogen, substituted or unsubstituted $C_{1-6}$ alkyl, or substituted or unsubstituted $C_{3-6}$ cycloalkyl.

Still other non-limiting exemplary polymers of the present invention include one or more of the following

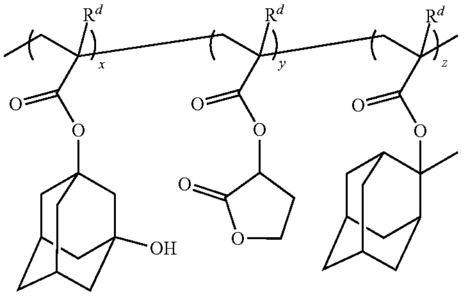

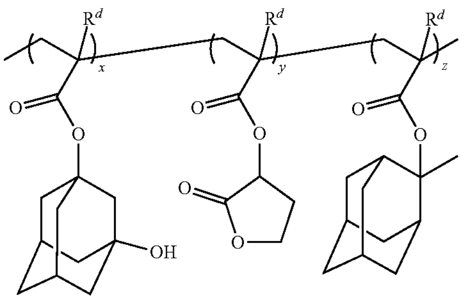

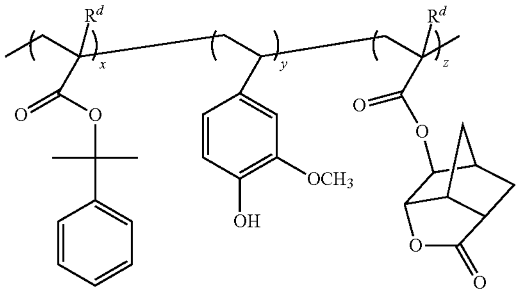

-continued

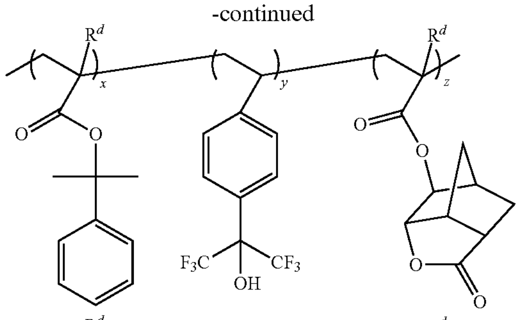

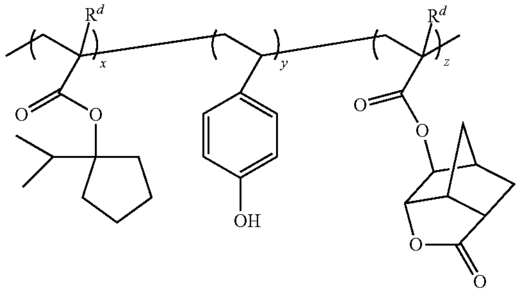

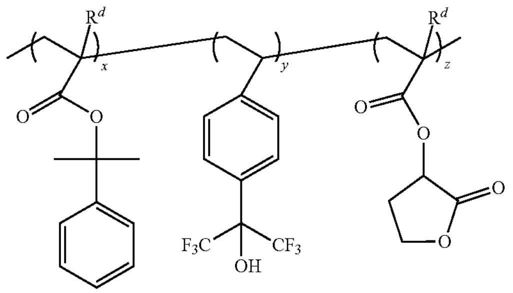

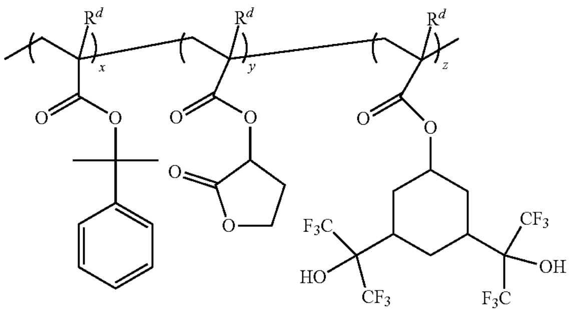

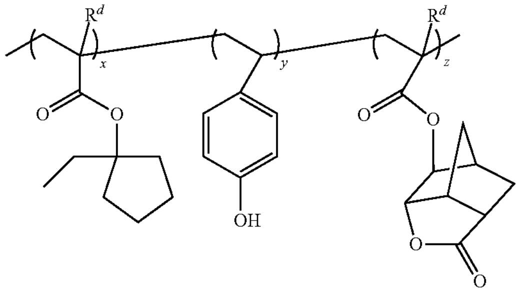

-continued

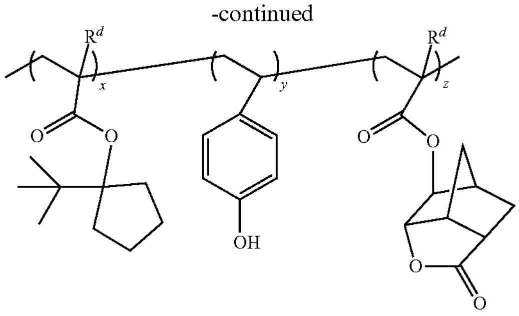

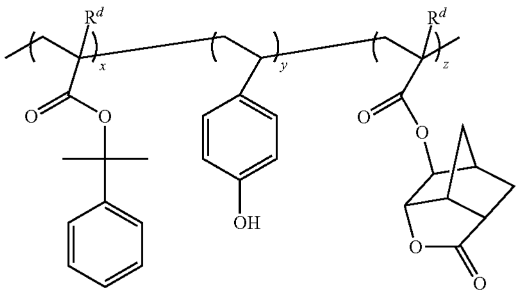

wherein each of x, y and z is a molar fraction of an associated repeating unit, wherein the sum of the molar fractions for each polymer adds up to 1, and wherein each $R^d$ is independently hydrogen, halogen, substituted or unsubstituted $C_{1-6}$ alkyl, or substituted or unsubstituted $C_{3-6}$ cycloalkyl.

The polymer typically has a weight average molecular weight ($M_w$) from 1,000 to 50,000 Dalton (Da), preferably from 2,000 to 30,000 Da, more preferably 3,000 to 20,000 Da, and still more preferably from 4,000 to 15,000 Da. The polydispersity index (PDI) of the first polymer, which is the ratio of M, to number average molecular weight ($M_w$) is typically from 1.1 to 3, and more typically from 1.1 to 2. Molecular weight values are determined by gel permeation chromatography (GPC) using polystyrene standards.

In the photoresist compositions of the invention, the polymer is typically present in the photoresist composition in an amount from 10 to 99.9 wt %, typically from 25 to 99 wt %, and more typically from 50 to 95 wt %, based on total solids of the photoresist composition. It will be understood that total solids includes the polymer(s), PAGs, and other non-solvent components.

The polymers may be prepared using any suitable method (s) in the art. For example, one or more monomers corresponding to the repeating units described herein may be combined, or fed separately, using suitable solvent(s) and initiator, and polymerized in a reactor. For example, the polymer may be obtained by polymerization of the respective monomers under any suitable conditions, such as by heating at an effective temperature, irradiation with actinic radiation at an effective wavelength, or a combination thereof.

The photoresist composition may further include a photoacid generator (PAG). The PAG may be in ionic or non-ionic form. The PAG may be in polymeric or non-polymeric form. In polymeric form, the PAG may be present as a moiety in a repeating unit of a polymer that is derived from a polymerizable PAG monomer.

Suitable PAG compounds maybe of the formula $G^+A^-$, wherein $G^+$ is a photoactive cation and $A^-$ is an anion that can generate a photoacid. The photoactive cation is preferably chosen from onium cations, preferably iodonium or sulfonium cations such as those described above with respect to the inventive photoactive compounds (e.g., those of Formulae (7a) and/or (7b)). Particularly suitable anions include those whose conjugated acids have a pKa of from −15 to 10. The anion is typically an organic anion having a sulfonate group or a non-sulfonate-type group, such as sulfonamidate, sulfonimidate, methide, or borate.

In some aspects, the anion of the PAG does not include and is free of —F, —$CF_3$, or —$CF_2$— groups. It should be understood that "free of —F, —$CF_3$, or —$CF_2$— groups" means that the anion of the PAG excludes groups such as —$CH_2CF_3$ and —$CH_2CF_2CH_3$. In still other aspects, the anion of the PAG is free of fluorine (i.e., does not contain a fluorine atom and is not substituted by a fluorine-containing group). In some aspects, the photoacid generator is free of fluorine (i.e., both the photoactive cation and the anion are free of fluorine).

Exemplary organic anions having a sulfonate group include one or more of the following:

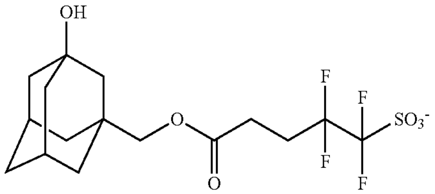

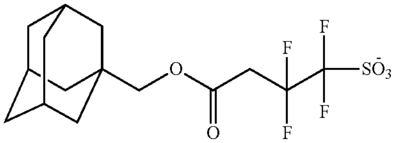

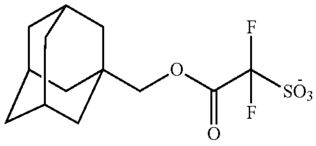

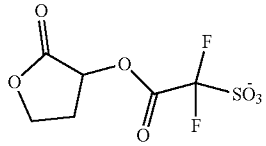

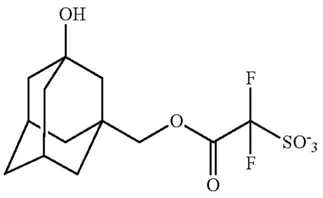

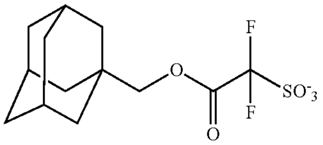

-continued

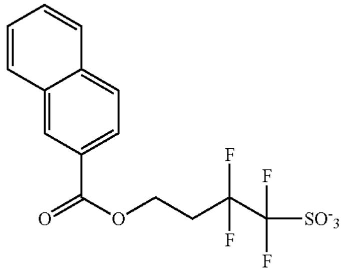

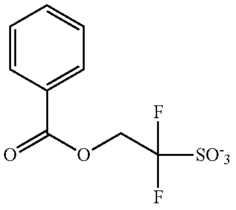

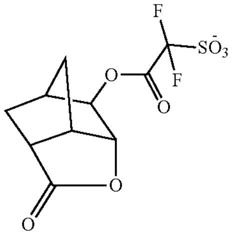

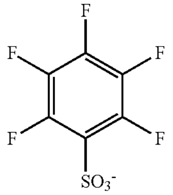

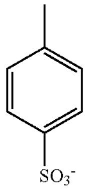

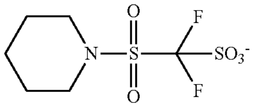

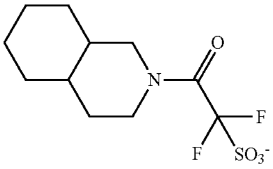

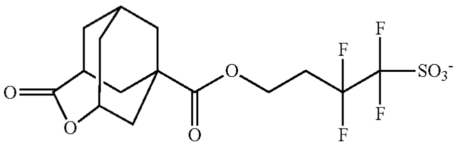

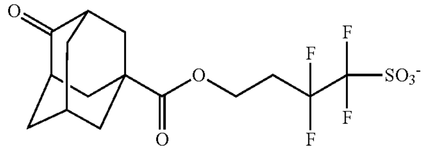

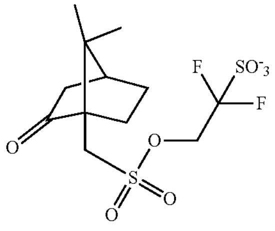

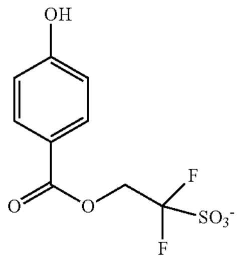

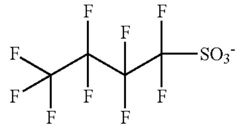

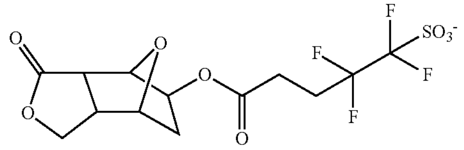

-continued

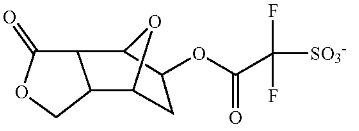

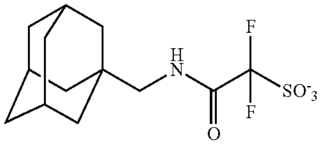

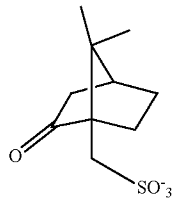

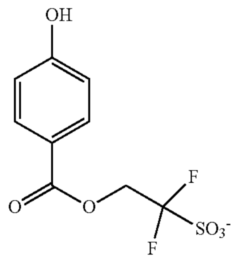

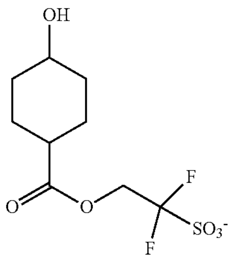

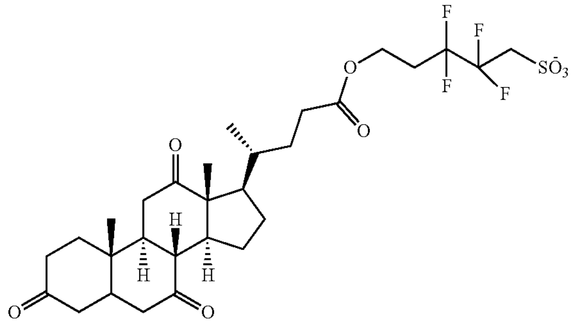

Exemplary non-sulfonated anions include one or more of the following:

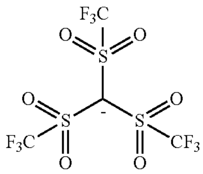

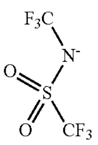

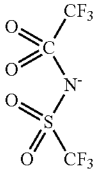

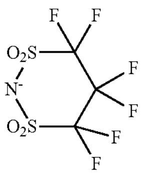

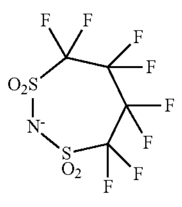

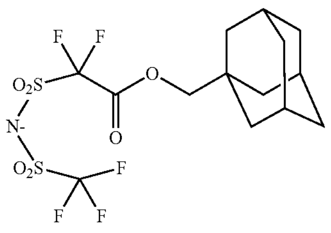

-continued

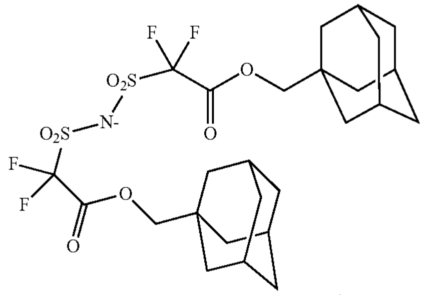

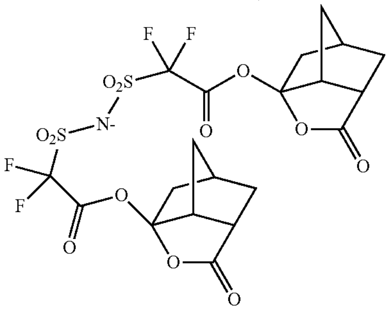

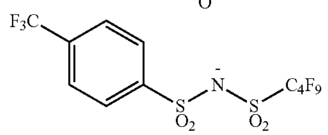

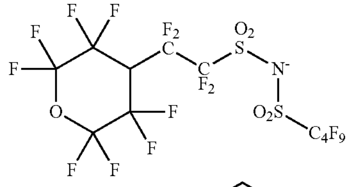

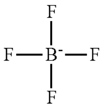

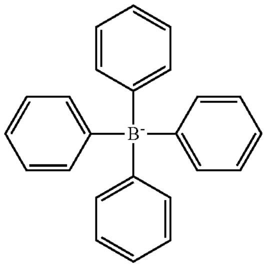

Commonly used onium salts may include, for example, triphenylsulfonium trifluoromethanesulfonate, (p-tert-butoxyphenyl)diphenylsulfonium trifluoromethanesulfonate, tris(p-tert-butoxyphenyl)sulfonium trifluoromethanesulfonate, triphenylsulfonium p-toluenesulfonate; di-t-butyphenyliodonium perfluorobutanesulfonate, and di-t-butyphenyliodonium camphorsulfonate. Other useful PAG compounds are known in the art of chemically amplified photoresists and include, for example: non-ionic sulfonyl compounds, for example, 2-nitrobenzyl-p-toluenesulfonate, 2,6-dinitrobenzyl-p-toluenesulfonate, and 2,4-dinitrobenzyl-p-toluenesulfonate; sulfonic acid esters, for example, 1,2,3-tris(methanesulfonyloxy)benzene, 1,2,3-tris(trifluoromethanesulfonyloxy)benzene, and 1,2,3-tris(p-toluenesulfonyloxy)benzene; diazomethane derivatives, for example, bis(benzenesulfonyl)diazomethane, bis(p-toluenesulfonyl)diazomethane; glyoxime derivatives, for example, bis-O-(p-toluenesulfonyl)-α-dimethylglyoxime, and bis-O-(n-butanesulfonyl)-α-dimethylglyoxime; sulfonic acid ester derivatives of an N-hydroxyimide compound, for example, N-hydroxysuccinimide methanesulfonic acid ester, N-hydroxysuccinimide trifluoromethanesulfonic acid ester; and halogen-containing triazine compounds, for example, 2-(4-methoxyphenyl)-4,6-bis(trichloromethyl)-1,3,5-triazine, and 2-(4-methoxynaphthyl)-4,6-bis(trichloromethyl)-1,3,5-triazine. Suitable photoacid generators are further described in U.S. Pat. Nos. 8,431,325 and 4,189,323.

Typically, when the photoresist composition includes an additional non-polymeric PAG, the PAG is present in the photoresist composition in an amount of from 0.1 to 55 wt %, more typically 1 to 25 wt %, based on total solids of the photoresist composition. When present in polymeric form, the additional PAG is typically included in a polymer in an amount from 1 to 25 mol %, more typically from 1 to 8 mol %, or from 2 to 6 mol %, based on total repeating units in the polymer.

The photoresist composition further includes a solvent for dissolving the components of the composition and to facilitate its coating on a substrate. Preferably, the solvent is an organic solvent conventionally used in the manufacture of electronic devices. Suitable solvents include, for example: aliphatic hydrocarbons such as hexane and heptane; aromatic hydrocarbons such as toluene and xylene; halogenated hydrocarbons such as dichloromethane, 1,2-dichloroethane and 1-chlorohexane; alcohols such as methanol, ethanol, 1-propanol, iso-propanol, tert-butanol, 2-methyl-2-butanol, 4-methyl-2-pentanol, and diacetone alcohol (4-hydroxy-4-methyl-2-pentanone) (DAA); propylene glycol monomethyl ether (PGME); ethers such as diethyl ether, tetrahydrofuran, 1,4-dioxane, and anisole; ketones such as acetone, methyl ethyl ketone, methyl iso-butyl ketone, 2-heptanone, and cyclohexanone (CHO); esters such as ethyl acetate, n-butyl acetate, propylene glycol monomethyl ether acetate (PGMEA), ethyl lactate (EL), hydroxyisobutyrate methyl ester (HBM), and ethyl acetoacetate; lactones such as gamma-butyrolactone (GBL) and epsilon-caprolactone; lactams such as N-methyl pyrrolidone; nitriles such as acetonitrile and propionitrile; cyclic or non-cyclic carbonate esters such as propylene carbonate, dimethyl carbonate, ethylene carbonate, propylene carbonate, diphenyl carbonate, and propylene carbonate; polar aprotic solvents such as dimethyl sulfoxide and dimethyl formamide; water; and combinations thereof. Of these, preferred solvents include one or more of PGME, PGMEA, EL, GBL, HBM, CHO, DAA, or a combination thereof.

The total solvent content (i.e., cumulative solvent content for all solvents) in the photoresist compositions is typically from 40 to 99 wt %, for example, from 60 to 99 wt %, or from 85 to 99 wt %, based on total solids of the photoresist composition. The desired solvent content will depend, for example, on the desired thickness of the coated photoresist layer and coating conditions.

In some aspects, the photoresist composition may further include a material that comprises one or more base-labile groups (a "base-labile material"). As referred to herein, base-labile groups are functional groups that can undergo cleavage reaction to provide polar groups such as hydroxyl, carboxylic acid, sulfonic acid, and the like, in the presence of an aqueous alkaline developer after exposure and post-exposure baking steps. The base-labile group will not react significantly (e.g., will not undergo a bond-breaking reaction) prior to a development step of the photoresist composition that comprises the base-labile group. Thus, for instance, a base-labile group will be substantially inert during pre-exposure soft-bake, exposure, and post-exposure bake steps. By "substantially inert" it is meant that ≤5%, typically 1%, of the base-labile groups (or moieties) will decompose, cleave, or react during the pre-exposure soft-bake, exposure, and post-exposure bake steps. The base-labile group is reactive under typical photoresist development conditions using, for example, an aqueous alkaline photoresist developer such as a 0.26 normal (N) aqueous solution of tetramethylammonium hydroxide (TMAH). For example, a 0.26 N aqueous solution of TMAH may be used for single puddle development or dynamic development, e.g., where the 0.26 N TMAH developer is dispensed onto an imaged photoresist layer for a suitable time such as 10 to 120 seconds (s). An exemplary base-labile group is an ester group, typically a fluorinated ester group. Preferably, the base-labile material is substantially not miscible with and has a lower surface energy than the first and/or second polymers and other solid components of the photoresist composition. When coated on a substrate, the base-labile material can thereby segregate from other solid components of the photoresist composition to a top surface of the formed photoresist layer.

In some aspects, the base-labile material may be a polymeric material, also referred to herein as a base-labile polymer, which may include one or more repeating units comprising one or more base-labile groups. For example, the base-labile polymer may comprise a repeating unit comprising 2 or more base-labile groups that are the same or different. A preferred base-labile polymer includes at least one repeating unit comprising two or more base-labile groups, for example a repeating unit comprising 2 or 3 base-labile groups.

The base-labile polymer may be prepared using any suitable methods in the art. For example, the base-labile polymer may be obtained by polymerization of the respective monomers under any suitable conditions, such as by heating at an effective temperature, irradiation with actinic radiation at an effective wavelength, or a combination thereof. Additionally, or alternatively, one or more base-labile groups may be grafted onto the backbone of a polymer using suitable methods.

In some aspects, the base-labile material is a single molecule comprising one more base-labile ester groups, preferably one or more fluorinated ester groups. The base-labile materials that are single molecules typically have a $M_r$ in the range from 50 to 1,500 Da.

When present, the base-labile material is typically present in the photoresist compositions in an amount of from 0.01 to 10 wt %, typically from 1 to 5 wt %, based on total solids of the photoresist composition.

Additionally, or alternatively, to the base-labile polymer, the photoresist compositions may further include one or more polymers in addition to and different from the polymer as described above.

For example, the photoresist compositions may include an additional polymer as described above but different in composition. Additionally, or alternatively, the one or more additional polymers may include those well known in the photoresist art, for example, those chosen from polyacrylates, polyvinylethers, polyesters, polynorbornenes, polyacetals, polyethylene glycols, polyamides, polyacrylamides, polyphenols, novolacs, styrenic polymers, polyvinyl alcohols, or combinations thereof.

The photoresist composition may further include one or more additional, optional additives. For example, optional additives may include actinic and contrast dyes, anti-striation agents, plasticizers, speed enhancers, sensitizers, photo-decomposable quenchers (PDQ) (and, also known as photo-decomposable bases), basic quenchers, thermal acid generators, surfactants, and the like, or combinations thereof. If present, the optional additives are typically present in the photoresist compositions in an amount of from 0.01 to 10 wt %, based on total solids of the photoresist composition.

PDQs generate a weak acid upon irradiation. The acid generated from a photo-decomposable quencher is not strong enough to react rapidly with acid-labile groups that are present in the resist matrix. Exemplary photo-decomposable quenchers include, for example, photo-decomposable cations, and preferably those also useful for preparing strong acid generator compounds, paired with an anion of a weak acid (pKa>1) such as, for example, an anion of a $C_{1-20}$ carboxylic acid or $C_{1-20}$ sulfonic acid. Exemplary carboxylic acids include formic acid, acetic acid, propionic acid, tartaric acid, succinic acid, cyclohexanecarboxylic acid, benzoic acid, salicylic acid, and the like. Exemplary sulfonic acids include p-toluene sulfonic acid, camphor sulfonic acid and the like. In a preferred embodiment, the photo-decomposable quencher is a photo-decomposable organic zwitterion compound such as diphenyliodonium-2-carboxylate.

The PDQ may be in non-polymeric or polymer-bound form. The polymerized units containing the photo-decomposable quencher are typically present in an amount from 0.1 to 30 mole %, preferably from 1 to 10 mole % and more preferably from 1 to 2 mole %, based on total repeating units of the polymer.

Exemplary basic quenchers include, for example, linear aliphatic amines such as tributylamine, trioctylamine, triisopropanolamine, tetrakis(2-hydroxypropyl)ethylenediamine: n-tert-butyldiethanolamine, tris(2-acetoxy-ethyl) amine, 2,2',2",2'"-(ethane-1,2-diylbis(azanetriyl))tetraethanol, 2-(dibutylamino)ethanol, and 2,2',2"-nitrilotriethanol; cyclic aliphatic amines such as 1-(tert-butoxycarbonyl)-4-hydroxypiperidine, tert-butyl 1-pyrrolidinecarboxylate, tert-butyl 2-ethyl-1H-imidazole-1-carboxylate, di-tert-butyl piperazine-1,4-dicarboxylate, and N-(2-acetoxy-ethyl) morpholine; aromatic amines such as pyridine, di-tert-butyl pyridine, and pyridinium; linear and cyclic amides and derivatives thereof such as N,N-bis(2-hydroxyethyl)pivalamide, N,N-diethylacetamide, $N^1,N^1,N^3,N^3$-tetrabutylmalonamide, 1-methylazepan-2-one, 1-allylazepan-2-one, and tert-butyl 1,3-dihydroxy-2-(hydroxymethyl)propan-2-ylcarbamate; ammonium salts such as quaternary ammonium salts of sulfonates, sulfamates, carboxylates, and phosphonates; imines such as primary and secondary aldimines and ketimines; diazines such as optionally substituted pyrazine, piperazine, and phenazine; diazoles such as optionally substituted pyrazole, thiadiazole, and imidazole; and optionally substituted pyrrolidones such as 2-pyrrolidone and cyclohexyl pyrrolidine.

The basic quenchers may be in non-polymeric or polymer-bound form. When in polymeric form, the quencher may be present in repeating units of the polymer. The repeating units containing the quencher are typically present in an amount of from 0.1 to 30 mole %, preferably from 1 to 10 mole % and more preferably from 1 to 2 mole %, based on total repeating units of the polymer.

Exemplary surfactants include fluorinated and non-fluorinated surfactants and can be ionic or non-ionic, with non-ionic surfactants being preferable. Exemplary fluorinated non-ionic surfactants include perfluoro $C_4$ surfactants such as FC-4430 and FC-4432 surfactants, available from 3M Corporation; and fluorodiols such as POLYFOX PF-636, PF-6320, PF-656, and PF-6520 fluorosurfactants from Omnova. In an aspect, the photoresist composition further includes a surfactant polymer including a fluorine-containing repeating unit.

Patterning methods using the photoresist compositions of the invention will now be described. Suitable substrates on which the photoresist compositions can be coated include electronic device substrates. A wide variety of electronic device substrates may be used in the present invention, such as: semiconductor wafers; polycrystalline silicon substrates; packaging substrates such as multichip modules; flat panel display substrates; substrates for light emitting diodes (LEDs) including organic light emitting diodes (OLEDs); and the like, with semiconductor wafers being typical. Such substrates are typically composed of one or more of silicon, polysilicon, silicon oxide, silicon nitride, silicon oxynitride, silicon germanium, gallium arsenide, aluminum, sapphire, tungsten, titanium, titanium-tungsten, nickel, copper, and gold. Suitable substrates may be in the form of wafers such as those used in the manufacture of integrated circuits, optical sensors, flat panel displays, integrated optical circuits, and LEDs. Such substrates may be any suitable size. Typical wafer substrate diameters are 200 to 300 millimeters (mm), although wafers having smaller and larger diameters may be suitably employed according to the present invention. The substrates may include one or more layers or structures which may optionally include active or operable portions of devices being formed.

Typically, one or more lithographic layers such as a hardmask layer, for example, a spin-on-carbon (SOC), amorphous carbon, or metal hardmask layer, a CVD layer such as a silicon nitride (SiN), a silicon oxide (SiO), or silicon oxynitride (SiON) layer, an organic or inorganic underlayer, or combinations thereof, are provided on an upper surface of the substrate prior to coating a photoresist composition of the present invention. Such layers, together with an overcoated photoresist layer, form a lithographic material stack.

Optionally, a layer of an adhesion promoter may be applied to the substrate surface prior to coating the photoresist compositions. If an adhesion promoter is desired, any suitable adhesion promoter for polymer films may be used, such as silanes, typically organosilanes such as trimethoxyvinylsilane, triethoxyvinylsilane, hexamethyldisilazane, or an aminosilane coupler such as gamma-aminopropyltriethoxysilane. Particularly suitable adhesion promoters include those sold under the AP™ 3000, AP™ 8000, and AP™ 9000S designations, available from DuPont Electronics & Industrial (Marlborough, Massachusetts).

The photoresist composition may be coated on the substrate by any suitable method, including spin coating, spray coating, dip coating, doctor blading, or the like. For example, applying the layer of photoresist may be accomplished by spin coating the photoresist in solvent using a coating track, in which the photoresist is dispensed on a spinning wafer. During dispensing, the wafer is typically spun at a speed of up to 4,000 rotations per minute (rpm), for example, from 200 to 3,000 rpm, for example, from 1,000 to 2,500 rpm, for a period from 15 to 120 seconds to obtain a layer of the photoresist composition on the substrate. It will be appreciated by those skilled in the art that the thickness of the coated layer may be adjusted by changing the spin speed and/or the total solids of the composition. A photoresist composition layer formed from the compositions of the invention typically has a dried layer thickness from 3 to 30 micrometers (m), preferably from greater than 5 to 30 m, and more preferably from 6 to 25 m.

The photoresist composition is typically next soft-baked to minimize the solvent content in the layer, thereby forming a tack-free coating and improving adhesion of the layer to the substrate. The soft bake is performed, for example, on a hotplate or in an oven, with a hotplate being typical. The soft bake temperature and time will depend, for example, on the photoresist composition and thickness. The soft bake temperature is typically from 80 to 170° C., and more typically from 90 to 150° C. The soft bake time is typically from 10 seconds to 20 minutes, more typically from 1 to 10 minutes, and still more typically from 1 to 2 minutes. The heating time can be readily determined by one of ordinary skill in the art based on the ingredients of the composition.

The photoresist layer is next pattern-wise exposed to activating radiation to create a difference in solubility between exposed and unexposed regions. Reference herein to exposing a photoresist composition to radiation that is activating for the composition indicates that the radiation can form a latent image in the photoresist composition. The exposure is typically conducted through a patterned photomask that has optically transparent and optically opaque regions corresponding to regions of the resist layer to be exposed and unexposed, respectively. Such exposure may, alternatively, be conducted without a photomask in a direct writing method, typically used for e-beam lithography. The activating radiation typically has a wavelength of sub-400 nm, sub-300 nm or sub-200 nm, with 248 nm (KrF), 193 nm (ArF), 13.5 nm (EUV) wavelengths or e-beam lithography being preferred. Preferably, the activating radiation is 248 nm radiation. The methods find use in immersion or dry (non-immersion) lithography techniques. The exposure energy is typically from 1 to 200 millijoules per square centimeter ($mJ/cm^2$), preferably from 10 to 100 $mJ/cm^2$ and more preferably from 20 to 50 $mJ/cm^2$, dependent upon the exposure tool and components of the photoresist composition.

Following exposure of the photoresist layer, a post-exposure bake (PEB) of the exposed photoresist layer is performed. The PEB can be conducted, for example, on a hotplate or in an oven, with a hotplate being typical. Conditions for the PEB will depend, for example, on the photoresist composition and layer thickness. The PEB is typically conducted at a temperature from 70 to 150° C., preferably from 75 to 120° C., and a time from 30 to 120 seconds. A latent image defined by the polarity-switched (exposed regions) and unswitched regions (unexposed regions) is formed in the photoresist.

The exposed photoresist layer is then developed with a suitable developer to selectively remove those regions of the layer that are soluble in the developer while the remaining insoluble regions form the resulting photoresist pattern relief image. In the case of a positive-tone development (PTD) process, the exposed regions of the photoresist layer are removed during development and unexposed regions remain. Conversely, in a negative-tone development (NTD) process, the exposed regions of the photoresist layer remain, and unexposed regions are removed during development. Application of the developer may be accomplished by any suitable method such as described above with respect to application of the photoresist composition, with spin coating being typical. The development time is for a period effective to remove the soluble regions of the photoresist, with a time of from 5 to 60 seconds being typical. Development is typically conducted at room temperature.

Suitable developers for a PTD process include aqueous base developers, for example, quaternary ammonium hydroxide solutions such as TMAH, preferably 0.26 N TMAH, tetraethylammonium hydroxide, tetrabutylammonium hydroxide, sodium hydroxide, potassium hydroxide, sodium carbonate, potassium carbonate, and the like. Suitable developers for an NTD process are organic solvent-based, meaning the cumulative content of organic solvents in the developer is 50 wt % or more, typically 95 wt % or more, 98 wt % or more, or 100 wt %, based on total weight of the developer. Suitable organic solvents for the NTD developer include, for example, those chosen from ketones, esters, ethers, hydrocarbons, and mixtures thereof. The developer is typically 2-heptanone or n-butyl acetate.

A coated substrate may be formed from the photoresist compositions of the invention. Such a coated substrate includes: (a) a substrate having one or more layers to be patterned on a surface thereof; and (b) a layer of the photoresist composition over the one or more layers to be patterned.

The photoresist pattern may be used, for example, as an etch mask, thereby allowing the pattern to be transferred to one or more sequentially underlying layers by known etching techniques, typically by dry-etching such as reactive ion etching. The photoresist pattern may, for example, be used for pattern transfer to an underlying hardmask layer which, in turn, is used as an etch mask for pattern transfer to one or more layers below the hardmask layer. If the photoresist pattern is not consumed during pattern transfer, it may be removed from the substrate by known techniques, for example, oxygen plasma ashing. The photoresist compositions may, when used in one or more such patterning processes, be used to fabricate semiconductor devices such as memory devices, processor chips (CPUs), graphics chips, optoelectronic chips, LEDs, OLEDs, as well as other electronic devices.

The invention is further illustrated by the following non-limiting examples.

EXAMPLES

Synthesis Examples

The synthetic reactions were performed under a nitrogen atmosphere. All chemicals were used as received from commercial suppliers and used without further purification. Proton nuclear magnetic resonance ($^1H$-NMR) spectra for all compounds were obtained either on a 500-megahertz (MHz) NMR spectrometer. The chemical shifts are reported in 6 (parts per million, ppm) relative to an internal tetramethylsilane standard. Multiplicities are indicated by singlet (s), doublet (d), triplet (t), multiplet (m), doublet of doublets (dd), doublet of triplets (dt), triplet of triplets (tt), or broad singlet (br).

Synthesis of Q1

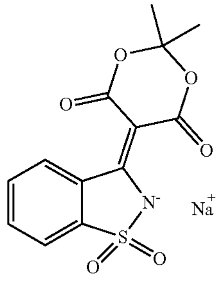

A

+

-continued

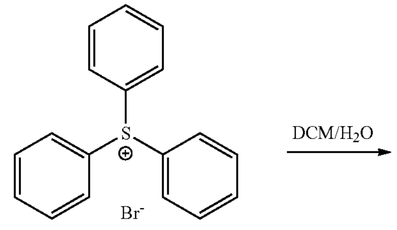

B

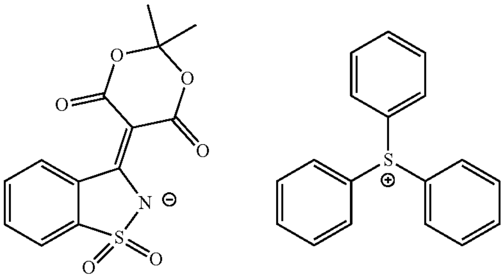

Q1

To a solution of compound A (0.66 grams (g), 1.99 millimoles (mmol)) in 10 milliliters (mL) of dichloromethane (DCM) was added compound B (0.68 g, 2 mmol) and 10 mL of deionized (DI) water. The resulting biphasic reaction mixture was stirred for one hour at room temperature. The organic layer was then separated and washed with 5 mL of DI water. The organic layer was again separated after washing, and the solvent was removed under a reduced pressure to yield 1.1 g (96%) of product Q1 as a beige solid. $^1$H-NMR (δ, dimethylsulfoxide-$d_6$ (DMSO-$d_6$)) 7.92-7.75 ppm (17H, m), 7.64-7.56 ppm (2H, m), and 1.64 ppm (6H, m).

Synthesis of Q2

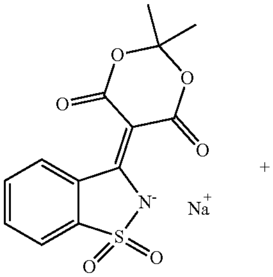

A

+

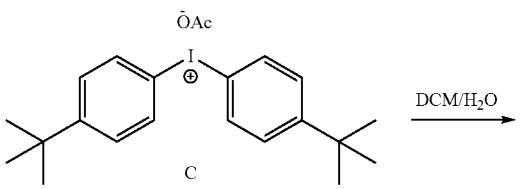

C

-continued

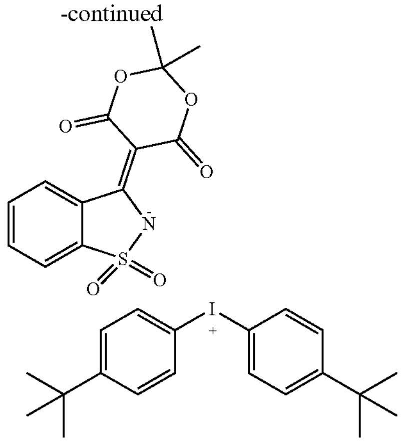

Q2

To a solution of compound A (0.66 g, 1.99 mmol) in 10 mL of DCM was added compound C (0.9 g, 2 mmol) and 10 mL of DI water. Following a similar procedure as for the synthesis of Q1 yielded 1.3 g (93%) of product Q2 as a white-orange solid. $^1$H-NMR (δ, DMSO-$d_6$) 8.14 ppm (d, 4H), ppm (dd, 2H), 7.64-7.58 ppm (2H, m), 7.53 ppm (d, 4H), 1.64 ppm (6H, s), and 1.26 ppm (18H, s).

Synthesis of Q3

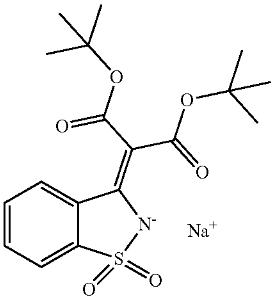

D

+

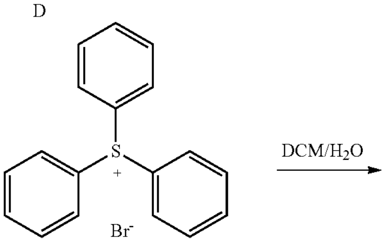

B

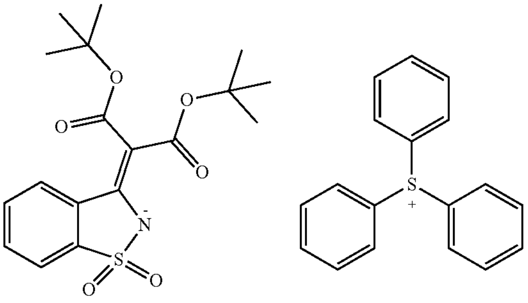

Q3

To a solution of compound D (0.5 g, 1.55 mmol) in 10 mL of DCM was added compound B (0.6 g, 3 mmol) and 10 mL of DI water. Following a similar procedure as for the synthesis of Q1 yielded 0.75 g (80%) of product Q3 as a light-yellow oil. $^1$H-NMR (δ, DMSO-$d_6$) 8.32 ppm (1H, d), 7.89-7.76 ppm (15H, m), 7.62 ppm (1H, d), 7.48 ppm (2H, m), and 1.43 ppm (18H, s).

Synthesis of Q4

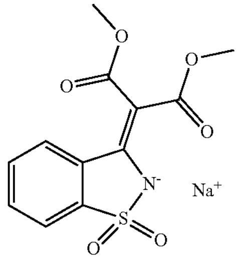

E

+

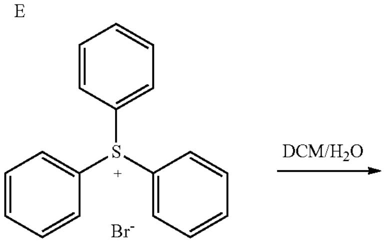

B

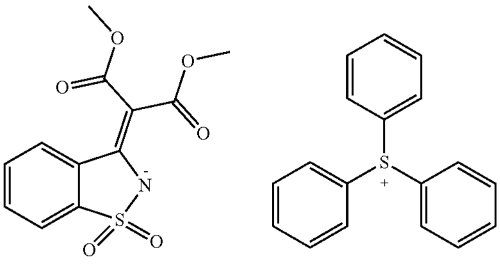

Q4

To a solution of compound E (2.0 g, 6.26 mmol) in 20 mL of DCM was added compound B (2.0 g, 5.82 mmol) and 20 mL of DI water. The resulting biphasic reaction mixture was then stirred for four hours at room temperature. The organic layer was separated and washed five times with 15 mL of DI water each time. The organic layer was separated again, and the solvent was removed under a reduced pressure to yield Q4 as a white solid. $^1$H-NMR (δ, DMSO-$d_6$) 7.69-7.59 ppm (17H, m), 7.64-7.42 ppm (2H, m), and 2.6 ppm (6H, s).

Synthesis of Q5

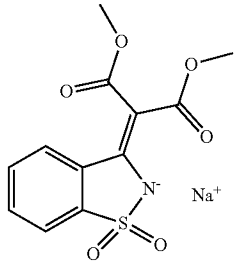

E

+

-continued

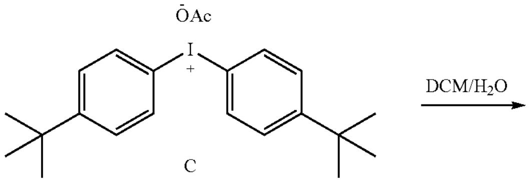

C

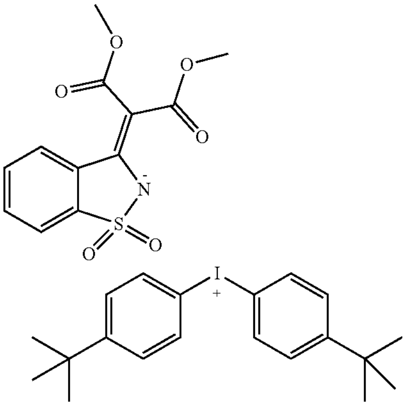

Q5

To a solution of compound E (1.0 g, 3.13 mmol) in 20 mL of DCM was added compound C (1.4 g, 3.9 mmol) and 20 mL of DI water. Following a similar procedure as for the synthesis of Q4 yielded Q5 as a white solid. $^1$H-NMR (δ, DMSO-$d_6$) 6.87 ppm (4H, d), 7.81 ppm (2H, m), 4.55 ppm (2H, M), 6.39 ppm (4H, d), and 1.29 ppm (18H, s).

Contrast Evaluation

Photoresist compositions were prepared by dissolving solid components in solvents using the materials and proportions set forth in Table 1 to a total solids content of 1.55 wt %. The amounts of the components are reported as wt % based on the total solids of the photoresist composition. The solvent system contained PGMEA (50 wt %) and diacetone alcohol (50 wt %). The resulting mixtures were shaken on a mechanical shaker and then filtered through a PTFE disk-shaped filter having a 0.2-micron pore size. 200 mm silicon wafers overcoated with a BARC stack (60 nm thick AR™ 3 antireflectant over 80 nm thick AR™ 40A antireflectant (DuPont Electronics & Industrial) were each spin-coated with a respective photoresist composition on a TEL Clean Track ACT 8 wafer track (TEL, Tokyo Electron Co.) and softbaked at 110° C. for 60 seconds to provide a photoresist layer with a target thickness of about 40 nm. The resist layer thickness was measured with a THERMA-WAVE OP7350. The wafers were exposed with 248 nm radiation on a CANON FPA-5000 ES4 scanner at exposure doses between 3 and 53 millijoules per square centimeter (mJ/cm$^2$). The wafers were post-exposure baked at 100° C. for 60 seconds, developed with MF™ CD26 TMAH developer (DuPont Electronics & Industrial) for 60 seconds, rinsed with DI water, and dried. Photoresist layer thickness measurements were made in exposed regions of the layer. A contrast curve for each wafer was generated and $E_0$ was determined from the contrast curves as described above. An additional contrast curve for each wafer was generated by plotting normalized photoresist layer thickness in the exposed regions vs. Log dose. Contrast (γ) was determined from the normalized contrast curve as the slope between the point of 80% and 20% photoresist film thickness. The results are shown in Table 1.

TABLE 1

| Example | Polymer | PAG | Photoactive Compound | $E_0$ (mJ/cm$^2$) | γ |
|---|---|---|---|---|---|
| 1 | P1 [76.71] | PAG-A [19.18] | Q1 [4.11] | 13.01 | 10.47 |
| 2 | P1 [76.00] | PAG-A [19.00] | Q2 [5.00] | 14.68 | 11.62 |
| 3 | P1 [76.32] | PAG-A [19.08] | Q3 [4.60] | 13.69 | 10.01 |
| 4* | P1 [78.10] | PAG-A [19.53] | CQ1 [2.37] | 12.55 | 7.18 |

*Denotes a comparative example.

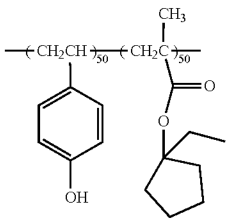

P1

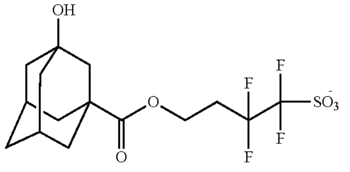

PAG-A

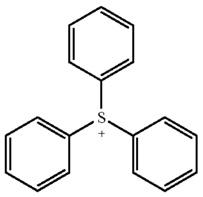

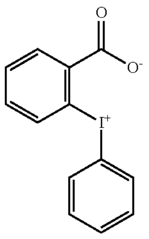

CQ1

Lithographic Evaluation

Photoresist compositions were prepared by dissolving the solid components in solvents using the materials and amounts set forth in Table 2, to a total solids content of 4.15 wt %. The amounts of the components are reported as wt % based on the total solids of the photoresist composition. The solvent system contained PGMEA (50 wt %) and diacetone alcohol (50 wt %). Each mixture was shaken using a mechanical shaker and then filtered through a PTFE disk-shaped filter having a pore size of 0.2 micron. Lithography was performed using a CLEAN TRAC ACT8 (TEL, Tokyo Electron Co.) wafer track. 200 nm wafers for photolithographic testing were coated with an AR™ 3 BARC (DuPont Electronics & Industrial) and softbaked at 205° C. for 60 seconds to give a 60 nm film. A coating of AR™ 40A BARC (DuPont Electronics & Industrial) was then disposed on the AR™ 3 layer and softbaked at 215° C. for 60 seconds to form a second BARC layer having a thickness of 80 nm. A photoresist composition was then coated onto the dual BARC stack and soft-baked at 110° C. for 60 seconds to give a photoresist film layer having a thickness of 120 nm.

The resulting wafers were exposed to 248 nm radiation using a CANON FPA-5000 ES4 scanner (NA=0.8, outer sigma=0.85, inner sigma=0.57) with a mask having a 1:1 CH pattern (200 nm linewidth). The exposed wafers were subjected to a post-exposure bake at 100° C. for 60 seconds, developed with a 0.26 N TMAH solution for 60 seconds, and then rinsed with DI water and spun dried to form photoresist patterns. Critical dimension (CD) linewidth measurements of the formed patterns were made using a HITACHI S-9380 CD-SEM. Localized critical dimension uniformity (LCDU) was determined based on the CD measurements. The sizing energy ($E_{size}$) and the LCDU data are shown in Table 2.

TABLE 2

| Example | Polymer | PAG | Photoactive compound | $E_{size}$ (mJ/cm$^2$) | LCDU (nm) |
|---|---|---|---|---|---|
| 5 | P1 [76.71] | PAG-A [19.18] | Q1 [4.11] | 124.0 | 5.38 |
| 6 | P1 [76.00] | PAG-A [19.00] | Q1 [5.00] | 118.6 | 5.17 |
| 7 | P1 [76.32] | PAG-A [19.08] | Q2 [4.60] | 113.2 | 5.2 |
| 8 | P1 [77.29] | PAG-A [19.32] | Q3 [3.39] | 104.1 | 5.88 |
| 9 | P1 [76.07] | PAG-A [19.02] | Q4 [4.91] | 108.8 | 5.28 |
| 10* | P1 [77.41] | PAG-A [19.35] | CQ2 [3.24] | 106.5 | 6.13 |

*Denotes comparative example.

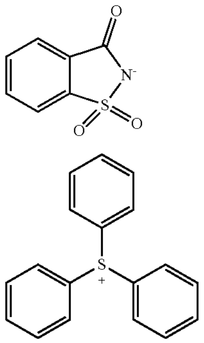

CQ2

While this disclosure has been described in connection with what is presently considered to be practical exemplary embodiments, it is to be understood that the invention is not limited to the disclosed embodiments, but, on the contrary, is intended to cover various modifications and equivalent arrangements included within the spirit and scope of the appended claims.

What is claimed is:

1. A photoactive compound, comprising:

an organic cation; and an anion represented by one of Formulae (5a) to (5c):

(5a)

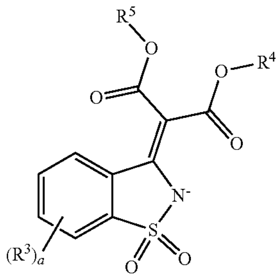

(5b)

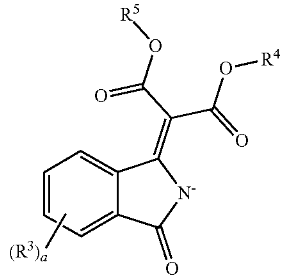

(5c)

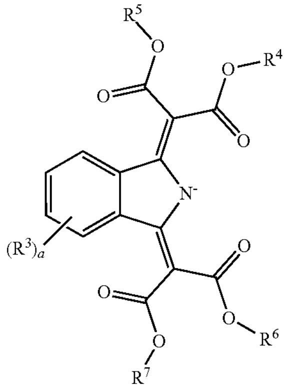

wherein, in Formulae (5a) to (5c), each $R^3$ is independently halogen, cyano, substituted or unsubstituted $C_{1-30}$ alkyl, substituted or unsubstituted $C_{3-30}$ cycloalkyl, substituted or unsubstituted $C_{3-30}$ heterocycloalkyl, substituted or unsubstituted $C_{6-30}$ aryl, substituted or unsubstituted $C_{7-30}$ arylalkyl, substituted or unsubstituted $C_{7-30}$ alkylaryl, substituted or unsubstituted $C_{6-30}$ aryloxy, substituted or unsubstituted $C_{3-30}$ heteroaryl, substituted or unsubstituted $C_{4-30}$ alkylheteroaryl, substituted or unsubstituted $C_{4-30}$ heteroarylalkyl, or substituted or unsubstituted $C_{3-30}$ heteroaryloxy;

each $R^3$ independently optionally further comprises one or more divalent linking groups as part of its structure;

a is an integer from 0 to 4;

when a is 2 or greater, adjacent two or more of $R^3$ together optionally form a ring;

in Formulae (5a) and (5b), $R^4$ and $R^5$ are each independently hydrogen, substituted or unsubstituted $C_{1-30}$ alkyl, substituted or unsubstituted $C_{3-30}$ cycloalkyl, substituted or unsubstituted $C_{3-30}$ heterocycloalkyl, substituted or unsubstituted $C_{6-30}$ aryl, substituted or unsubstituted $C_{7-30}$ arylalkyl, substituted or unsubstituted $C_{7-30}$ alkylaryl, substituted or unsubstituted $C_{6-30}$ aryloxy, substituted or unsubstituted $C_{3-30}$ heteroaryl, substituted or unsubstituted $C_{4-30}$ alkylheteroaryl, substituted or unsubstituted $C_{4-30}$ heteroarylalkyl, or substituted or unsubstituted $C_{3-30}$ heteroaryloxy;

$R^4$ and $R^5$ each independently optionally further comprises one or more divalent linking groups as part of its structure;

$R^4$ and $R^5$ together optionally form a ring;

in Formula (5c), $R^4$ to $R^7$ are each independently hydrogen, substituted or unsubstituted $C_{1-30}$ alkyl, substituted or unsubstituted $C_{3-30}$ cycloalkyl, substituted or unsubstituted $C_{3-30}$ heterocycloalkyl, substituted or unsubstituted $C_{6-30}$ aryl, substituted or unsubstituted $C_{7-30}$ arylalkyl, substituted or unsubstituted $C_{7-30}$ alkylaryl, substituted or unsubstituted $C_{6-30}$ aryloxy, substituted or unsubstituted $C_{3-30}$ heteroaryl, substituted or unsubstituted $C_{4-30}$ alkylheteroaryl, substituted or unsubstituted $C_{4-30}$ heteroarylalkyl, or substituted or unsubstituted $C_{3-30}$ heteroaryloxy;

$R^4$ to $R^7$ each independently optionally further comprises one or more divalent linking groups as part of its structure;

$R^4$ and $R^5$ together optionally form a ring, and/or $R^6$ and $R^7$ together optionally form a ring.

2. The photoactive compound of claim 1, wherein the anion represented by Formulae (5a) to (5c) is free of fluorine.

3. The photoactive compound of claim 1, wherein the anion comprises one or more acid labile groups.

4. The photoactive compound of claim 1, wherein the organic cation comprises an iodonium cation or a sulfonium cation.

5. A photoresist composition, comprising:

the photoactive compound of claim 1; and a polymer.

6. The photoresist composition of claim 5, further comprising a photoacid generator that is different from the photoactive compound, wherein the polymer comprises one or more acid labile groups.

7. The photoresist composition of claim 5, wherein the anion represented by Formulae (5a) to (5c) is free of fluorine.

8. The photoresist composition of claim 5, wherein the anion comprises one or more acid labile groups.

9. The photoresist composition of claim 5, wherein the organic cation comprises an iodonium cation or a sulfonium cation.

10. A patterning method, the method comprising:

applying a layer of the photoresist composition of claim 5 on a substrate to provide a photoresist composition layer;

pattern-wise exposing the photoresist composition layer to activating radiation to provide an exposed photoresist composition layer; and developing the exposed photoresist composition layer.

11. The method of claim 10, wherein the anion represented by Formulae (5a) to (5c) is free of fluorine.

12. The method of claim 10, wherein the anion comprises one or more acid labile groups.

* * * * *